US006177614B1

(12) United States Patent
Colasanti et al.

(10) Patent No.: US 6,177,614 B1
(45) Date of Patent: Jan. 23, 2001

(54) CONTROL OF FLORAL INDUCTION IN PLANTS AND USES THEREFOR

(75) Inventors: Joseph J. Colasanti, Kensington, CA (US); Venkatesan Sundaresan, Singapore (SG)

(73) Assignee: Cold Spring Harbor Laboratory, Cold Spring Harbor, NY (US)

( * ) Notice: Under 35 U.S.C. 154(b), the term of this patent shall be extended for 0 days.

(21) Appl. No.: 09/056,226

(22) Filed: Apr. 7, 1998

Related U.S. Application Data

(63) Continuation-in-part of application No. 09/000,640, filed on Dec. 30, 1997, which is a continuation-in-part of application No. 08/804,104, filed on Feb. 20, 1997, now abandoned, which is a continuation-in-part of application No. PCT/US96/03466, filed on Mar. 15, 1996, which is a continuation-in-part of application No. 08/406,186, filed on Mar. 16, 1995, now abandoned.

(51) Int. Cl.$^7$ ............... A01H 5/00; A01H 5/10; C12N 5/04; C12N 15/29; C12N 15/82

(52) U.S. Cl. ............ 800/290; 800/286; 800/320; 800/320.1; 435/412; 435/419; 435/69.1; 435/440; 435/468; 536/23.6; 536/24.5

(58) Field of Search ............... 800/286, 290, 800/298, 320, 320.1; 435/419, 412, 69.1, 440, 468; 536/23.6, 24.5

(56) References Cited

U.S. PATENT DOCUMENTS

| 4,513,532 | 4/1985 | Muirhead, Jr. et al. ............... 47/58 |
| 5,013,660 | 5/1991 | Kasuya et al. ............... 435/173 |
| 5,034,323 | 7/1991 | Jorgensen et al. ............... 435/172.3 |
| 5,098,843 | 3/1992 | Calvin et al. ............... 435/287 |
| 5,100,792 | 3/1992 | Sanford et al. ............... 435/172.1 |
| 5,107,065 | 4/1992 | Shewmaker et al. ............... 800/205 |
| 5,164,310 | 11/1992 | Smith et al. ............... 435/172.3 |
| 5,283,184 | 2/1994 | Jorgensen et al. ............... 435/172.3 |

FOREIGN PATENT DOCUMENTS

| 94/00472 | * 2/1994 | (WO) . |
| 96/14414 | 5/1996 | (WO) . |
| WO 97/25433 | 7/1997 | (WO) . |
| WO 98/37201 | 8/1998 | (WO) . |
| 96/34088 | 10/1998 | (WO) . |

OTHER PUBLICATIONS

Colasanti, J., et al., "The indeterminate Gene Encodes a Zinc Finger protein and Regulates a Leaf–Generated Signal Required for the Transition to Flowering in Maize", *Cell*, 93:593–603 (1998).

Sato, S., et al., "AC AB0005240", *EMBL Database*, Jul. 18, 1997.

Kuehn, C. et al., "*S. Tuberosum* mRNA for DNA/RNA Binding Protein" *Embl Sequence Database*, Rel. 41, Nov. 1, 1994, Assession No. X82327, XP002019118.

Chung, Yong–Yoon et al., "Early Flowering Reduced Apical Dominance Result from Ectopic Expression of a Rice Mads Box Gene" *Plant Molecular Biology*, 26: 657–665 (Oct. 1994) XP002004927.

Mladenovic, S. et al., "Recombinant DNA Technology in Maize Breeding. VI. Foreign Gene Influence on Maize Gemone Expression . . . " *Genetics 23(3)* : 191–203 (1991).

Landschuetze, V. et al., "Inhibition of Flower Formation by Antisense Repression of Mitochondrial Citrate Synthase in Transgenic Potato Plants Leads to a Specific Disintegration . . . " *The Embo Journal 14(4)*: 660–666 (Feb. 15, 1995) XP002019120.

Colasanti, J. et al., "Transposon Tagging of the Indeterminate Gene" *Maize Genetics Cooperation Newsletter 69:* 35 (1995) XP000610125.

Dean, C., "Signals to Green" *Trends in Genetics. Meeting Reports. Signaling in Plant Development,* Sep. 27–Oct. 1, 1995, 12(2): 74–75, Cold Spring Harbor Laboratory, USA, XP00201912.

Colasanti, J. et al., "idl–CSH Mutants Flower Earlier in the Presence of Ac" *Maize Genetics Cooperation Newsletter 69:* 36–37 (1995) XP000610126.

Colasanti, J. et al., "Isolation of New Alleles of Anther Ear and Indeterminate" *Maize Genetics Cooperation Newsletter 66:* 30–31 (1992) XP000660115.

Balcells, L. et al., "Transposons as Tools for the Isolation of Plant Genes" *Trends in Biotechnology 9(1)*:31–37 (Jan. 1991) XP002019122.

Law, C., et al., "Genes Controlling Flowering and Strategies for their Isolation and Characterization" *The Molecular Biology of Flowering* pp. 47–68, Jordan, B.R. (ed) C.A.B. International (1993) XP000610117.

An, G., "Regulatory Genes Controlling Flowering Time of Floral Organ Development" *Plant Molecular Biology 25:* 335–337 (1994) XP002019105.

Wright, P. E., "Solution Structures of DNA–binding Domains of Eukaryotic Transcription Factors," In *Transcriptional Regulation,* S. L. McKnight and K. R. Yamamoto, eds. (Cold Spring Harbor Laboratory Press) pp. 579–597 (1992).

Golds, T., et al., "Stable Plastid Transformation in PEG–treated Protoplasts of *Nicotiana tabacum,*" *Biotechnology 11:* 95–97 (1993).

Fedoroff, N. V., "Maize Transposable Elements," In *Mobile DNA*, M. Howe and D. Berg, eds., (Washington: ASM press) pp. 375–411 (1989).

Renaudin, J.–P., et al., "Cloning of Four Cyclins From Maize Indicates That Higher Plants Have Three Structurally Distinct Groups of Mitotic Cyclins," *PNAS 91:* 7375–7379 (1994).

(List continued on next page.)

Primary Examiner—David T. Fox
(74) Attorney, Agent, or Firm—Hamilton, Brook, Smith & Reynolds, P.C.

(57) ABSTRACT

The Id gene which controls flower evocation in maize plants is described. The maize nucleic acid is similar to that of genes encoding zinc-finger regulatory proteins in animals. Methods of isolation or preparation of other regulatory protein genes in plants and their uses are disclosed.

20 Claims, 11 Drawing Sheets

OTHER PUBLICATIONS

Gordon–Kamm, W.J., et al., "Transformation of Maize Cells and Regeneration of Fertile Transgenic Plants," *Plant Cell 2:* 603–618 (1990).

Ron, D. and Dressler, H., "pGSTag—A Versatile Bacterial Expression Plasmid for Enzymatic Labeling of Recombinant Proteins," *Biotech. 13(6):* 866–69 (1992). (Abstract).

Smith, D. B. and Johnson, K. S., "Single–step purification of polypeptides expressed in *Escherichia coli* as fusions with glutathione S–transferase," *Gene 67:* 31–40 (1988).

Callis, J., et al., "Introns Increase Gene Expression in Cultured Maize Cells," *Genes Dev. 1:* 1183–1200 (1987).

Gottschalk, W. and Wolff, G. "The Alteration of Flowering and Ripening Times," In *Induced Mutations in Plant Breeding,* (Springer–Verlag, Berlin, Heidelberg, New York Tokyo) Ch. 10 pp. 75–84 (1983).

Callis, J., et al., "Heat Inducible Expression of a Chimeric Maize hsp70–CAT Gene in Maize Protoplasts," *Plant Physiol. 88:* 965–968 (1988).

Urao, T., et al., "An Arabidopsis myb Homolog Is Induced by Dehydration Stress and Its Gene Product Binds to the Conserved MYB Recognition Sequence," *Plant Cell 5:* 1529–1539 (1993).

Lloyd, A.M., et al., "Arabidopsis and Nicotiana Anthocyanin Production Activated by Maize Regulators R and C1," *Science 258:* 1773–1775 (1992).

Vilardell, J., et al., "Gene Sequence, Developmental Expression, and Protein Phosphorylation of RAB–17 in Maize," *Plant Mol. Biol. 14:* 423–432 (1990).

Schoffl, F., et al., "The Function of Plant Heat Shock Promoter Elements in the Regulated Expression of Chimaeric Genes in Transgenic Tobacco," *Mol. Gen. Genet. 217:* 246–253 (1989).

Colasanti, J., et al., "Isolation and characterization of cDNA Clones Encoding a Functional p34$^{cdc2}$ homologue From *Zea mays,*" *Proc. Natl. Acad. Sci. USA 88:* 3377–3381 (1991).

Burr, B. and Szabo, V., "Experiments with idl," In *Maize Genetics Cooperation Newsletter 65:* 110 (Univ. of Missouri), (1991). (Abstract).

Neuffer, M. G. and Chao, S., "Instability in the An1 component of the idd*–2286A mutant," In *Maize Genetics Cooperation Newsletter 66:* 39 (Univ. of Missouri), (1992). (Abstract).

Neuffer, M. G. and Chao, S., "Indeterminate dwarf: an EMS–Induced double mutant," In *Maize Genetics Cooperation Newsletter 65:* 52 (Univ. of Missouri), (1991). (Abstract).

Neuffer, M. G. and Chang, M. T., "id mutants from EMS treatment," In *Maize Genetics Cooperation Newsletter 63:* 62 (Univ. of Missouri) 1989. (Abstract).

Colasanti, J. and Sundaresan, V., "Analysis of Indeterminate Gene Function in Maize," In *Cold Spring Harbor Laboratory Annual Report* pp. 140–141 (1994). (Abstract).

Bernier, G., "The Control of Floral Evocation and Morphogenesis," *Ann. Rev. Plant Physiol. Plant Molec. Biol. 39:* 75–219 (1988).

Singleton, W.R., "Inheritance of Indeterminate Growth in Maize," *J. Heredity 37:* 61–64 (1946).

Galinat, W. C. and Naylor, A. W., "Relation of Photoperiod to Inflorescence Proliferation in *Zea Mays* L.," *Am. J. Bot. 38:* 38–47 (1951).

Hake, S., et al., "Cloning Knotted, the Dominant Mutant in Maize Using Ds2 as a Transposon Tag," *EMBO J. 8:* 15–22 (1989).

Freeling, M. and Walbot, V., eds., *The Maize Handbook,* Ch. 21, pp. 197–208; Ch. 91, pp. 541–544; Ch. 105, pp. 595–598; Ch. 109, pp. 613–615; and Ch. 122, pp. 677–684 (Springer–Verlag, New York, Inc.) (1994).

Walbot, V., "Strategies for Mutagenesis and Gene Cloning Using Transposon Tagging and T–DNA Insertional Mutagenesis" *Annual Review of Plant Physiology and Plant Molecular Biology 43(1):* 49–82 (Jan. 1, 1992) XP000607244.

Theres, N. et al., "Cloning of the Bz2 Locus of *Zea Mays* Using the Transposable Element Ds as a Gene Tag" *Molecular and General Genetics 209:*193–197 (1987) XP000611383.

Database WPI, Section Ch, Week 9243, Derwent Publications Ltd., Longon, GB; Class C06, AN 92–354683 XP002018484 and JP,A,04 258 292 (Japan Tobacco Inc.), Sep. 14, 1992 (Abstract).

Federoff, N. V., et al., "Cloning of the bronze locus in maize by a simple and generalizable procedure using the transposable controlling element Activator (Ac)," *PNAS 81:* 3825–3829 (1984).

Lee, I., et al., "Isolation of Luminidependens: A Gene Involved in the Control of Flowering Time in Arabidopsis," *The Plant Cell 6:* 75–83 (Jan. 1994).

Kano–Murakami, Y. et al., "A Rice Homeotic Gene, OSHI, Causes Unusual Phenotypes in Transgenic Tobacco," *FEBS Letters 334(3):* 365–368, FEBS Letters (Nov. 1993).

Lewin, R., "When Does Homology Mean Something Else?" *Science 237:* 1570.

Reeck, G.R., " 'Homology' in Proteins and Nucleic Acids: A Terminology Muddle and a Way Out of It," *Cell 50:* 667 (Aug. 1987).

Colasanti, J. and Sundaresan, V. "Long Distance Signals for Flowering: Genetic Evidence that the Maize Indeterminate Gene Regulates A Floral Stimulus" *Flowering Newsletter 24:*4–9 (Nov., 1997).

Colasanti, J. and Sundaresan, V. "Control of the Transition of Flowering" Current Opinion in Biotechnology 7:145–149 (1996).

Kuhn, C. and Frommer, W.B., "A novel zinc finger protein encoded by a couch potato homologue from Solanum tuberosum enables a sucrose transport–deficient yeast strain to grow on sucrose" *Mol. Gen. Genet. 247:*759–763 (1995).

Napoli et al. Plant Cell 2:279–289, Apr. 1990.*

Smith et al. Nature 334:724–726, Aug. 1988.*

Newman et al. Plant Physiol. 106:1241–1255, 1997.*

* cited by examiner

Genomic Sequence of the *id1* gene 1
61

GACGACAGACGATGCAGATGATGATGCTCTCTGATCTCTCGTCTGACGACCACGAGGCCAC
TGGATCCAGCTCCTATGGCGGGGACATGGCCAGCTACGCCCTCAGCCCTCTCTTCCTCGCA
CCGGCGGCCTCGGCCACCGCGCCGCTGCCGCCACCTCCGCAGCCGCCGGCCGAGGAGCTC
ACCAACAAGCAGGCCGCGGGCGGCGGCAAGAGGAAGAGAAGCCAGCCGGGGAACCCAGGTA
CGTAGTAGTTAATTGGCTGACCAATCACGCCGACCGATGCACCTAATTAATGAATCAATGT
GCTACAAATAAATTAAAACCAAAAGACCCCGGCGCGGAGGTGATCGCGCTGTCGCCGCGCA
CGCTGGTGGCGACGAACCGGTTCGTGTGCGAGATCTGCAACAAGGGGTTCCAGCGGGACCA
GAACCTGCAGCTGCACCGCCGGGGCCACAACCTCCCCTGGAAGCTCCGCCAGCGCAGCAGC
CTCGTCGTCCCGTCGTCGTCGGCGGCGGCAGGCTCCGGCGGCAGGCAGCAGCAGCAGCAGG
GCGAGGCCGCGCCGACGCCGCCGCGTAAGCGCGTCTACGTCTGCCCCGAGCCCACGTGCG
TGCACCACGACCCGGCGAGGTACGTATGCACGGTCCTGCTCCTGCATATATGCGAGGGAAT
GCTAGCGACATAGCATAACATCTCATCGATCCATCCATCCATCCATCCATCCATCCATCCA
TCCATCCATCCATCAGAGCTCTGGGGGACTTGACTGGGATCAAGAAGCACTTCTCGCGGAA
GCACGGGGAGAAGCGGTGGTGCTGCGAGCGCTGCGGGAAGCGCTACGCCGTGCAGTCGGAC
TGGAAGGCGCACGTCAAGGGGTGTGGCACGCGCGAGTACCGCTGCGACTGCGGCATCCTCT
TCTCCAGGTACATCTCATCTCATGATCACCGTGCACATATGCATGGACGACGTGTGCTTTG
CTGTAATTGTAAACGCTGATCATTTTTACTAACAACCATGCTGGATATAATAGCCTAATCT
CTCACCGGACGGATCGAGAGAAAACCTAGCTAGACGGGATCGATCGGTCCAGCAGGTTGCC
GCCGACGACTGTTCCATCGATCGAGCCTGTTAATTTAGTCATAAAAAGGATCGAGCATATG
CATGTATATGAACTATCTTCCTTCACTGACCAACATCATATCATGCATGGAGCTAGCTAGT
TAATCAGTACATATACTCCTATATATACATAGGTTTTCAAGAACAGTGGGTGATTCTGAAG
CAACCTAAATATATATAGATACCAAAAAANATATGAAGTCATCAGCACGATCTGCGAGCGG
GTACGGTTCTTGAACTCTTCTGATGGTTGCAGTAATACCGGCCAACAAAAATATATTATAT
ATTTATCGTCCGCTAGTTGATTTTTAAACTAAATGCGCACTGATAAAAAAGAAGGGTTGG
AGTACTATATATACAAGAGCATGTGGCCTTCAGTTACAATTTTAGGGTTTCCATGCATCCT
GTCATAAAACTATTTGCATGATCACATCCCTATATATCGGGATACTACTGTTGTGAAAAAA
CCATGAGTCCCTGGTCAAACCAGTATATGTACATGCAATATGTTTATTGCATGCATATTTG
GGAATGAACATCCTCTGCCTGCACCAACTTTATGGCAGTACGTCCATGTGGCCATCATGAC
ACATTCCCTTCAAAAATGGAACATATATAGCTACAGCATATGAAGCAATTGAAGAGTACTT
TAATTGTGAAATAGTACTACTGCAAGTATATATATATGTAGTAGCACAACAGTCGAATAAT
GCAGTGCATTAGATATAGTAGTGAAGTTAAGAGTTAGTTTCCAAATCTTTTACTAGAGAGA

FIGURE 2A

```
GCATAAAAAATCTATAAAAAATTCTAATTCAACTTCTAATGTATCTTATGTTAAGAAAGGG
GTATATATAAAAGAGTAAATTCTGTCATTAGATACATCGTTAGCAGTAGTACCACTGAAT
TTAATTACGTCCTATACACACGCGCACACACATGCATGCATGCATCTGCATGCTTCTTTTC
AGTAGTGATCACAAAGGAAACTGACAAAGAACCTAGCTAATCATAGGACGCAGCTTTTCG
TCAGCAAAGTTAAACGAAACTTTACATGCATGGATTGCATTGAGTACTCACGCATGTGCAC
GTCAACACGCGCACACATATAGTATATTAACATAGTACTTTATATACCAACTAATTAATAA
AGTCATTGACTCCTCTGTCCTCTGGTCATTTGTTTAGCTAATTAACCCGTTTCGTTTGATG
CATGCATGGTCTCTCTGGCGTGGTCGTGCAGGAAGGACAGCCTGCTCACGCACAGGGCCTT
CTGCGATGCCCTAGCAGAGGAGAGCGCGAGGCTTCTTGCAGCAGCAGCAAACAACGGCAGC
ACTATCACCACGACCAGCAGCAGCAACAACAATGATCTTCTCAACGCCAGCAATAATATCA
CGCCATTATTCCTCCCGTTCGCCAGCTCTCCTCCTCCTGTCGTCGTAGCGGCGGCACAAAA
CCCTAATAACACCCTCTTCTTCCTGCACCAAGAGCTGTCCCCCTTCCTGCAACCGAGGGTG
ACGATGCAACAACAACCCTCGCCCTATCTTGACCTCCATATGCACGTCGACGCCAGCATCG
TCACCACCACCGGTGGTCTCGCGGACGGCACGCCGGTCAGCTTTGGCCTCGCTCTGGACGG
CTCGGTGGCCACCGTCGGCCACCGGCGCCTCACTAGGGACTTCCTCGGTGTCGATGGTGGC
GGTCGTCAGGTCGAGGAGCTGCAGCTTCCACTGTGCGCCACAGCAGCCGCAGCAGGTGCCA
GCCGCACCGCCAGCTGCGCCACCGACCTGACAAGGCAGTGCCTCGGCGGCCGGCTGCCGCC
GGTCAACGAGACCTGGAGCCACAACTTCTAGGCCCGCTATATACTTCAAGCTGCATTGAGA
CTTTGAGAGACGAATGAACGGAACACCCAAACTGCATGCACTCTAGCTTGAAGAGCAAACC
AAAACTGGAGTAGCAAGTATGGTGCACTACTGTTGTTAATTTACCTTAATTTATTGATCTC
TGGTTAGTTCTGTTTTCATTTAGGGCAATGCGGGCTAGCTAATTAATTCGATGTGCACAAC
TTTTGATGAATGGACCATAAAGTTTATCTTGTTGCTTTTTTTTTGTTTGATTATGTTTCGC
TGCACACCCATGTGTTCTCATAATGGTATGTCGAAAGAAATAGATGATATACTAATATAAC
CATATCAGTCTAAACAACATGAATAAAGATTCAATCAAGAGGAGTGGCACATGCATGGTTA
CTGATGGTGGTACGGAGTCATCGATAAGTGGTAGTGGAGGAAAAGCTTGGTGCAAACGGCG
ATGAATACAACGACACGTATAGCACCGTTTAACTTGGATGAAAGACGACTCGTCGTGGAAG
TTGAGAGCAGTCATGCAAAGAACACTTTCCAAAAACCTTATTAAATATGTCCTCTATCTGT
GCAAGGTTAGAAAGATGAGAATTATGGAGATCTACTCTCCTGAATCCTGATTGGTGATGCA
CGTAAATGCTCAGGATGAAGAGGCTATGACGTCAGTGCAACATTGAGAAGTGAAAAATACT
AATTTATATCTTAAGATTTTTCAAAGTAGGAGCTC
```

Amino acid sequence of *Id1* gene

```
                                                              50
MQMMLSDLS SDDHEATGSS SYGGDMASYA LSPLFLAPAA SATAPLPPPP
QPPAEELTNK QAAGGGKRKR SQPGNPDPGA EVIALSPRTL VATNRFVCEI
CNKGFQRDQN LQLHRRGHNL PWKLRQRSSL VVPSSSAAAG SGGRQQQQG
EAAPTPPRKR VYVCPEPTCV HHDPARALGD LTGIKKHFSR KHGEKRWCCE
RCGKRYAVQS DWKAHVKGCG TREYRCDCGI LFSRKDSLLT HRAFCDALAE
ESARLLAAAA NNGSTITTTS SSNNNDLLNA SNNITPLFLP FASSPPPVVV
AAAQNPNNTL FFLHQELSPF LQPRVTMQQQ PSPYLDLHMH VDASIVTTTG
GLADGTPVSF GLALDGSVAT VGHRRLTRDF LGVDGGGRQV EELQLPLCAT
AAAAGASRTA SCATDLTRQC LGGRLPPVNE TWSHNF
                                                             436
```

Feature

Zinc-finger #1    From a.a. #98 to #118

Zinc-finger #2    From a.a. #199 to #219

FIG. 3

ORF (Open Reading Frame): encodes a portion of a protein homologous to zinc-finger regulatory proteins

FIG.6

```
            HFSNPALNRRWVCHACG      Drosophila

ALGDLTGIKKHFSRKHGEKRWCCERCGK   maize ORF

HLKLHKGEKPFPCSQCGK     Xenopus

AYSRLENLKTHLRSHTGEKPYVCEHEG    human

KHKKIHKGQQYYTCRDCEK    mouse
```

FIG. 7

| allele | | | | mutant phenotype | leaf # |
|---|---|---|---|---|---|
| Normal id | G I L F S R K D<br>GGCATCCTCTTCTCCAGGAAGGAC --- | | | none | 12-14 |
| id1-m1 | GGCATCCTCTTCTCCAGG ▶[Ds2]◀ TCTCCAGG ---<br>(1.3 kb) | | | −Ac: severe<br>+Ac: variable | >25<br>16->25 |
| id1-X1 | G I L F S R<br>GGCATCCTCTTCTCCAG | (+7 bp) | L Q<br>ACTCCAGG --- | severe | >25 |
| id1-X2 | G I L F S<br>GGCATCCTCTTCTCC | (+5 bp) | T P<br>ACTCCAGG --- | severe | >25 |
| id1-XD17 | G I L F S R<br>GGCATCCTCTTCTCCAG | (+7 bp) | L Q<br>ACTCCAGG --- | severe | >25 |
| id1-XD27 | G I L F<br>GGCATCCTCTTCTC | (−10 bp) | --- | severe | >25 |
| id1-XG9 | G I L F S<br>GGCATCCTCTTCTCC | (+3 bp) | S R<br>TCCAGG --- | moderate | 19 |

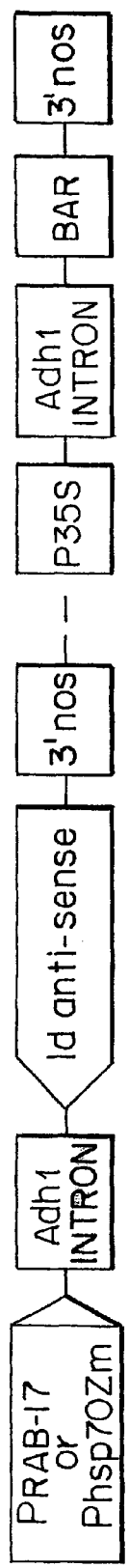
FIG. IOA
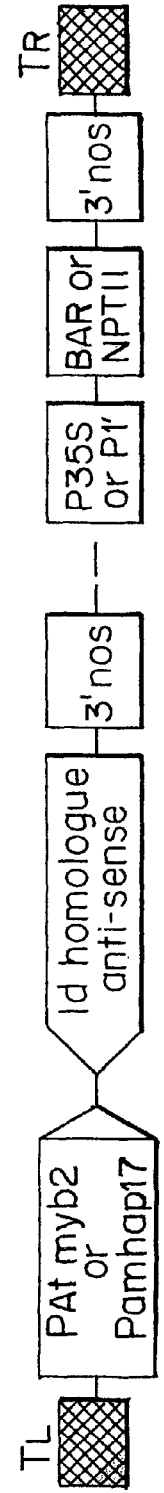
FIG. IOB

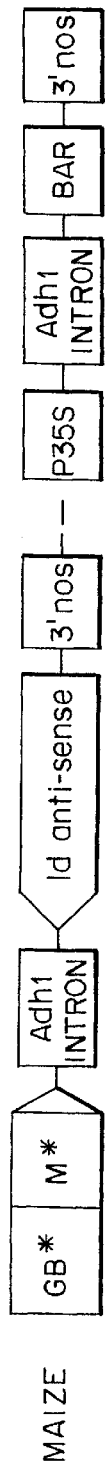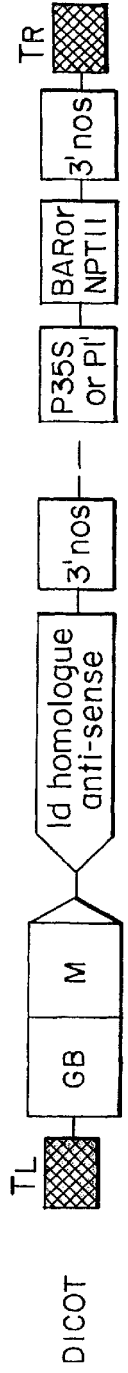
FIG. IIA  
FIG. IIB  
FIG. IIC  
FIG. IID
\* GB = GAL4 Binding Site (17mers as described in Ma, J. et al., supra)
\*\* M = Minimal Promoter (TATA Box)

CONTROL OF FLORAL INDUCTION IN PLANTS AND USES THEREFOR

RELATED APPLICATIONS

This application is a continuation-in-part of U.S. patent application Ser. No. 09/000,640 filed Dec. 30, 1997, which is a continuation-in-part of U.S. patent application Ser. No. 08/804,104, filed Feb. 20, 1997, now abandonded, which is a continuation-in-part of PCT/US96/03466, filed Mar. 15, 1996, which, in turn, is a continuation-in-part of U.S. patent application Ser. No. 08/406,186, filed Mar. 16, 1995, now abandoned. The teachings of the referenced Applications are expressly incorporated herein by reference in their entirety.

GOVERNMENT SUPPORT

The invention described herein was made in whole or in part with government support under USDA Award No. 91-37304-6701 and USDA Award No. 94-37304-1004 awarded by the United States Department of Agriculture. The United States Government has certain rights in the invention.

BACKGROUND OF THE INVENTION

Higher plants have a life cycle that consists of a period of vegetative growth followed by reproductive development. Reproduction in angiosperms is a developmental process that begins with floral induction (evocation). This is the point in time at which the shoot apical meristem, the set of dividing cells that gives rise to most of the plant parts above the roots, stops making leaves and starts making flowers. Bernier, G. (1988) The control of floral evocation and morphogenesis. *Ann. Rev. Plant. Physiol. Plant Molec. Biol.* 39:175–219. Almost nothing is known, however, about the molecular and genetic controls that induce a plant to flower.

There is a great need for more information about the regulatory elements in plants. Increased knowledge of these elements would significantly improve our understanding of the underlying mechanism by which genes induce reproductive development in plants.

SUMMARY OF THE INVENTION

This invention identifies and provides isolated DNA which comprises an Id gene of a maize plant, or a portion thereof, which demonstrates Id gene function. The invention further provides RNA encoded by the DNA of the Id or id* alleles and portions thereof, and antisense (complementary) DNA and/or RNA or portions thereof. Nucleic acids, referred to as Id homologues or equivalents, which 1a) show greater than 50% homology (sequence similarity) or that hybridize under moderate stringency conditions to a portion consisting of 20 or more contiguous nucleotide bases of the Id gene or 1b) show a 70% or greater homology or that hybridize under moderate stringency conditions to the Id gene, and 2) demonstrate Id-type (initiation of reproduction phase) function are also encompassed by this invention. Nucleic acid probes and primers to detect and/or amplify regulatory genes in other plants are included as well. Thus, the DNA of this invention comprises an Id gene, or a portion thereof, the Id gene comprising all or a portion of SEQ ID NO:1, or homologous DNA.

The present invention further encompasses polypeptides which are Id proteins or portions of an Id protein of plant origin, including the polypeptides herein described. Id proteins from all plant species or homologues demonstrating a similar regulatory function (reproductive induction) are encompassed by this invention and the term Id protein as used herein. Amino acid sequences that demonstrate 80% or greater homology to the amino acid sequences described herein are considered homologous polypeptides.

In another aspect, this invention relates to antibodies which bind the polypeptides described herein. Such antibodies can be used to locate sites of regulatory activity in plants. Fusion proteins comprising the Id protein and an additional peptide, such as a protein tag, can also be used to detect sites of Id protein/protein interaction in plants.

In a further aspect, this invention provides methods for producing plants with selected times of transition from the vegetative to the flowering stage. Applicants have created a new allele of the id gene, id*, which, when an active Ac transposable element is present, causes plants to stop vegetative growth and to flower earlier than do other id mutants. As shown herein, the id*/id* plants with an active Ac element exhibit fewer vegetative nodes and flower earlier than id*/id* plants without an Ac element or plants encoding the id allele.

The present invention relates to a new mutant of the id gene which encodes a product that alters flower induction in plants and provides a nucleotide sequence of part of the Id SacI 4.2 kb fragment derived from maize Chromosome 1. Also included is DNA which hybridizes under high stringency conditions to the SacI fragment or a portion thereof and an RNA transcribed from or corresponding to either of said aforementioned DNA. Preferably the DNA is that shown in FIG. 4 (SEQ ID NO:3).

In another aspect, this invention provides methods for producing new id alleles and methods for detecting other Id alleles or other regulatory genes in plants. Homologues of the Id gene can be identified throughout the plant kingdom, including the multicellular and unicellular algae.

In yet another aspect of this invention are provided plants, seeds, plant tissue culture, and plant parts which contain DNA comprising an altered or exogenously introduced Id allele or portion of an Id allele that alters the timing of flower induction in the subsequent growth of the plant, seeds, plant tissue culture, and/or plant part.

The present invention also relates to transgenic plants in which the time of floral evocation is altered. Transgenic plants are provided in which the time period from germination to flowering is shorter than it is in the corresponding naturally-occurring or wild type (native) plant. Alternatively, plants are provided in which flowering is delayed or absent. As used herein, the term transgenic plants includes plants that contain either DNA or RNA which does not naturally occur in the wild type (native) plant or known variants, or additional or inverted copies of the naturally-occurring DNA and which is introduced as described herein, and any of the above-described alterations which result in plants having altered floral evocation times. Such transgenic plants include, in one embodiment, transgenic plants which are angiosperms, both monocotyledons and dicotyledons. Transgenic plants include those into which DNA has been introduced and their progeny, produced from seed, vegetative propagation, cell, tissue or protoplast culture, or the like.

Transgenic plants of the present invention contain DNA which encodes all or a portion of a protein essential for floral evocation and, when present in plant cells, results in altered floral evocation, either earlier cessation of vegetative growth and initiation of flowering than in untransformed plants of the same variety, or in later flowering or the absence of floral induction. The DNA can be exogenous DNA in a sense or antisense orientation which encodes a protein required for floral induction or exogenous DNA which has been altered in such a manner that it encodes an altered form of a protein required for floral induction. Directed or targeted mutagenesis of a plant's endogenous DNA responsible for initiation of flowering can also result in altered floral induction. Exogenous DNA encoding an altered protein required for floral evocation and endogenous DNA required for floral evocation which has been mutated by directed mutagenesis differ from the corresponding wild type (naturally-occurring) DNA in that these sequences contain a substitution, deletion or addition of at least one nucleotide and encode proteins which differ from the corresponding wild type protein by at least one amino acid residue. (As used herein, the term "nucleotide" is used interchangeably with "nucleic acid".) Insertion of genetic elements, such as Ds sequences with or without active Ac sequences, are of particular use. Exogenous DNA is introduced into plant cells of the target plant by well-known methods, such as Agrobacterium-mediated transformation, microprojectile bombardment, microinjection or electroporation (see below). Such cells carrying the introduced exogenous DNA or endogenous Id DNA mutated by direct mutagenesis can be used to regenerate transgenic plants which have altered floral induction, therefore becoming sources of additional plants either through seed production or non-seed asexual reproductive means (i.e., cuttings, tissue culture, and the like).

The present invention also relates to methods of producing plants with altered floral induction times, exogenous DNA or RNA whose presence in a plant results in altered floral induction, and vectors or constructs which include DNA or RNA useful for producing recombinant plants with altered floral development. Seeds produced by plants which contain exogenous DNA or RNA encoding a protein which is required for floral induction, such as Id DNA in the sense orientation or exogenous DNA which has been altered in such a manner that it encodes an altered form of a protein required for floral development, such as altered id* DNA, are also the subject of the present invention.

The work described herein makes available an Id gene, the genomic sequence, or a portion thereof, which has been determined by the Applicants, and which has an important role in the induction of flowering of plants. The gene is derived from a monocot, specifically, maize, one of the most commercially valuable grasses. The polypeptide encoded by this gene is a regulatory protein that causes a switch from vegetative growth to the development of reproductive organs in maize. In addition, in maize as in many other plants, the effects of this protein marks the beginning of senescence in these plants.

Corn requires more rainfall than wheat and most maize cultivars need a long growing season. The work described herein also makes it possible to grow maize and other latitude-dependent plants which require long growing seasons before flowering can take place to be grown in geographic regions with short growing seasons. Thus, the plants can be induced to flower and set seed prior to the first frost. Similarly, flower induction can be prolonged for short-season plants grown in areas with long periods of warm weather. As a result of the extra vegetative mass and carbohydrate, these plants can produce more and/or larger flowers and, consequently, more seed. Or, plants can even be prevented from flowering, thus providing nutritious silage biomass.

In another aspect, this invention provides a means to eliminate the need for detasseling in the production of maize and sorghum hybrids.

BRIEF DESCRIPTION OF THE FIGURES

FIGS. 2A–2B are the genomic sequence (SEQUENCE ID NO:1) comprising DNA of the Id gene.

FIG. 3 is the deduced amino acid sequence of FIGS. 2A–2B (SEQ ID NO:2). The Ds2 transposon insertion occurs at nucleotide 914.

FIG. 6 is a comparison of the maize Id gene ORF to known zinc-finger proteins of eukaryotic animal species. These eukaryotes include Drosophila (SEQ ID NO: 5), maize (SEQ ID NO: 6), Xenopus (SEQ ID NO: 7), human (SEQ ID NO: 8), and mouse (SEQ ID NO: 9).

FIG. 7 shows the frame shifts produced by the excision of Ds2 from the Id gene ORF, resulting in four null mutants, id1-X1, id1-X2, id1-XD17 and id1-XD27. The nucleic acid and encoded amino acid sequences, respectively, for these mutants are designated as follows: SEQ ID NO: 11 and SEQ ID NO: 12 (id1-X1); SEQ ID NO: 13 and SEQ ID NO: 14 (id1-X2); SEQ ID NO: 11 and SEQ ID NO: 12 (id1-XD17); and SEQ ID NO: 15 and SEQ ID NO: 16 (id1-XD27). FIG. 7 also shows the Id allele id1-XG9, (SEQ ID NO: 17, nucleic acid) and (SEQ ID NO: 18, amino acid), that resulted when the Ds2 transposon excised and left 3 basepairs (hereinafter, "bp"), resulting in the addition of a single serine residue. FIG. 7 additionally shows the insertion of the Ds2 transposon, "id1-m1", (SEQ ID NO: 10).

FIGS. 10A–10B depicts schematic representations of Id antisense constructs in which a drought induced promoter is fused with the Id cDNA for production of transgenic (FIG. 10A) monocots or (FIG. 10B) dicots to delay flowering in response to drought.

FIGS. 11A–11D depicts schematic representations of Id antisense constructs in which a GAL4 binding site (GB) is fused with the Id cDNA in a monocot (11A) or a dicot (11B), and a GAL4 gene is fused with a strong (CaMV 35s) or weak promoter in a monocot (11C) or a dicot (11D), for production of transgenic plants in which flowering is absent or delayed.

DETAILED DESCRIPTION OF THE INVENTION

Figure 1:
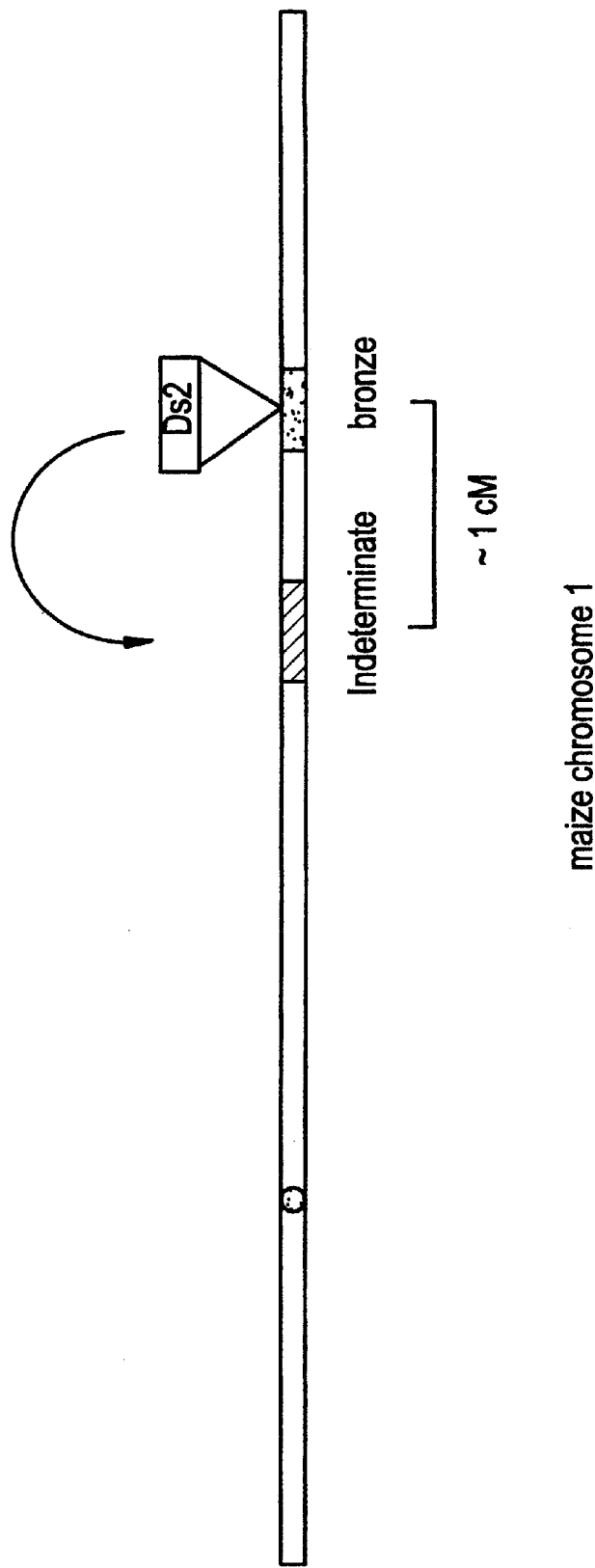
FIG. 1 is a map of Chromosome 1 showing the location of the indeterminate and Bz2 (bronze kernel pigmentation) genes, and the site of transposon insertion for Ds2.

During reproductive growth the plant enters a program of floral development that culminates in fertilization, followed by the production of seeds. Senescence may or may not follow. A maize plant (or its close relative, sorghum) is normally programmed to generate a particular number of vegetative structures (e.g. leaves), followed by reproductive structures (flowers), and to eventually undergo senescence of the plant. Maize (*Zea mays*) plants that are homozygous for the indeterminate (id) mutation of the Id gene, however, are defective in the execution of this program and exhibit several developmental phenotypes: 1) The vegetative to reproductive transition is altered such that the vegetative phase is prolonged, resulting in plants with an extensive (or indeterminate) lifespan; i.e., they flower much later than normal plants, or not at all. 2) The vegetative phase expands into the reproductive phase of development and causes abnormal flower development; i.e., the female flower (ear) exhibits vegetative characteristics and is usually sterile, and the male flower (tassel) can undergo a complete developmental reversion such that new vegetative shoots emerge from tissues that have characteristics of floral tissue. In the latter case, terminally differentiated cells that comprise floral tissues redifferentiate into vegetative tissue and resume proliferative growth. Singleton, W. R., *J. Heredity*, 37:61–64 (1946); Galinat, W. C. and Naylor, A. W. (1951) *Am. J. Bot.* 38:38–47. These phenotypes suggest that the function of the normal Id gene is to suppress vegetative growth and signal the beginning of reproductive growth at a specific time during the life cycle of the plant. Loss of Id function results in the failure to make this transition and causes prolonged vegetative development.

Normal Id function, therefore, is important in the vegetative to reproductive transition in maize; i.e., floral induction or evocation. Genetic and molecular data suggest that the Id gene encodes a regulatory protein that plays a crucial role in the switch from vegetative to reproductive development in maize and other plants. Understanding the mechanism of this regulation provides a basis for producing specialized plants designed to flower and produce seed independent of native internal controls or environmental effects. In fact, it is possible that the same mechanism utilizing a homologue of the Id gene controls spore production in non-seed plants, such as the algae.

The term "Id" means the normal (wild type) gene of maize; whereas, "id" refers to an altered (mutant) form of the Id gene. Isolated DNA of plant origin which encodes polypeptides which trigger initiation of the reproductive phase in the plant can be genomic or cDNA. DNA included in the present invention is from monocots, which are grasses; specifically described is the Id gene from maize.

Applicants have created a new allele of the id mutation that results from the disruption of normal Id gene function by the insertion of the 1.3 kb transposable element Dissociation (Ds) into the gene. A clone containing a portion of the mutated id gene, id*, was then isolated by the technique of transposon tagging using Ds as the tag. Hake, et al., *EMBO J.*, 8:15–22 (1989); Federoff et al. (1984) *PNAS* 81:3825–3829. Preliminary sequence analysis of a portion of the gene (id* and Id) indicates that Id contains regions that are homologous to a class of transcription factor found in all eukaryotic organisms.

A transposable genetic element (transposon) is a piece of DNA that moves from place to place in an organism's genome. It is excised from one site and inserted at another site, either on the same chromosome or on a different one. The movement of a transposable element can generate mutations or chromosomal rearrangements and thus affect the expression of other genes.

Transposons Ac and Ds constitute a family of related transposable elements present in maize. Fedoroff, N. (1989) *Maize Transposable Elements*. In *Mobile DNA*, M. Howe and D. Berg, eds, Washington: ASM press. Ac is able to promote its own transposition or that of Ds to another site, either on the same chromosome or on a different one. Ds cannot move unless Ac is present in the same cell. Ac is an autonomous transposable element and Ds is a nonautonomous element of the same family.

The insertion of Ds into a locus of a gene results in a mutation at that locus. For example, the C locus in maize kernels makes a factor required for the synthesis of a purple pigment. Insertion of the Ds element in the locus inactivates the gene, rendering the kernel colorless. This mutation is unstable, however. In the presence of the active Ac element, Ds is transposed away from the locus in some cells and the mutation reverts, giving rise to sectors of pigmented cells and thus to a purple-spotted kernel.

The Applicants have used a derivative of the Ds transposable element, Ds2, to produce a new mutant of the Id gene. This was accomplished by excision of Ds2 (in the presence of active Ac) from a nearby gene on chromosome 1 and its subsequent insertion into the Id gene to produce id*.

Through several generations of out-crosses and back-crosses, id* was introduced into genetic backgrounds with or without active Ac elements. Data from these experiments show that id*/id* plants with active Ac elements have a less severe phenotype than those with no Ac or Id plants; i.e., they exhibit fewer vegetative nodes and flower earlier. This result is expected if the Ac element mediates somatic excision of the Ds2 element from the id* allele during growth. Excision would restore Id function and result in partial restoration of normal development. Furthermore, the observation that these plants do not show patterns of defined sectoring (i.e., sharp demarcation of normal tissue juxtaposed to mutant tissue) suggests that Id acts non-cell-autonomously. This result implies that the Id gene product is either itself a diffusible factor, or that it regulates the production of a diffusible factor.

The above experiments, in which the effect of Ac on the flowering of id* plants was studied, demonstrate that the flowering time of the maize plant can be regulated quantitatively by the amount of id gene product available. Wild type (Id) plants from these families flowered at 9 to 11 weeks after planting. Plants homozygous for id*, with no Ac present, had not flowered after 25 weeks, at which time the experiment was terminated due to frost. The plants that were homozygous for id* and which also had Ac, flowered anywhere from 15 to 22 weeks. Excisions of Ds occur in these plants due to the presence of Ac. These excisions restore Id function, and result in sufficient Id gene product to cause the plants to flower earlier than the plants with no Ac, but not sufficient Id gene product to cause them to flower as early as the wild type plants. The large range in flowering times presumably reflects the intrinsic variability in the timing and frequencies of Ds excisions from plant to plant. Fedoroff (1989), supra.

Another experiment examined the Ac effect on id* plants more closely. The element Ac shows a "negative dosage" effect; that is, one copy of Ac causes many more Ds excisions than two or more copies of Ac. Fedoroff (1989), supra. The effect of Ac dosage on id* plants was determined by planting seeds which were homozygous for id* and which carried no Ac, one Ac, or two or more Ac elements per genome. If the amount of available Id product regulates flowering, then id* plants containing two or more Ac elements were expected to flower later than id* plants with one Ac element but earlier than id* plants with no Ac element. This experiment was performed under greenhouse conditions in which wild type controls flowered after producing 12 to 13 leaves. None of the id* plants lacking Ac elements flowered even after 24 leaves were produced. Of the id* plants containing two or more Ac elements, 12.5% flowered after producing 21 to 23 leaves, whereas 87.5% of the plants did not flower even after producing 24 leaves. In contrast, 90% of the plants carrying one Ac element flowered after producing 16 to 24 leaves. The results demonstrate that id* plants containing one Ac element (those with the greatest number of Ds excisions and therefore, the greatest amount of Id product) flower earlier than plants with more than one Ac element (although not as early as wild type plants). The results also suggest that varying the amount of functional Id gene product, e.g., by varying the frequency of Ds excision through different doses of Ac, can induce a quantitative variation of the time of flowering.

Figure 4:
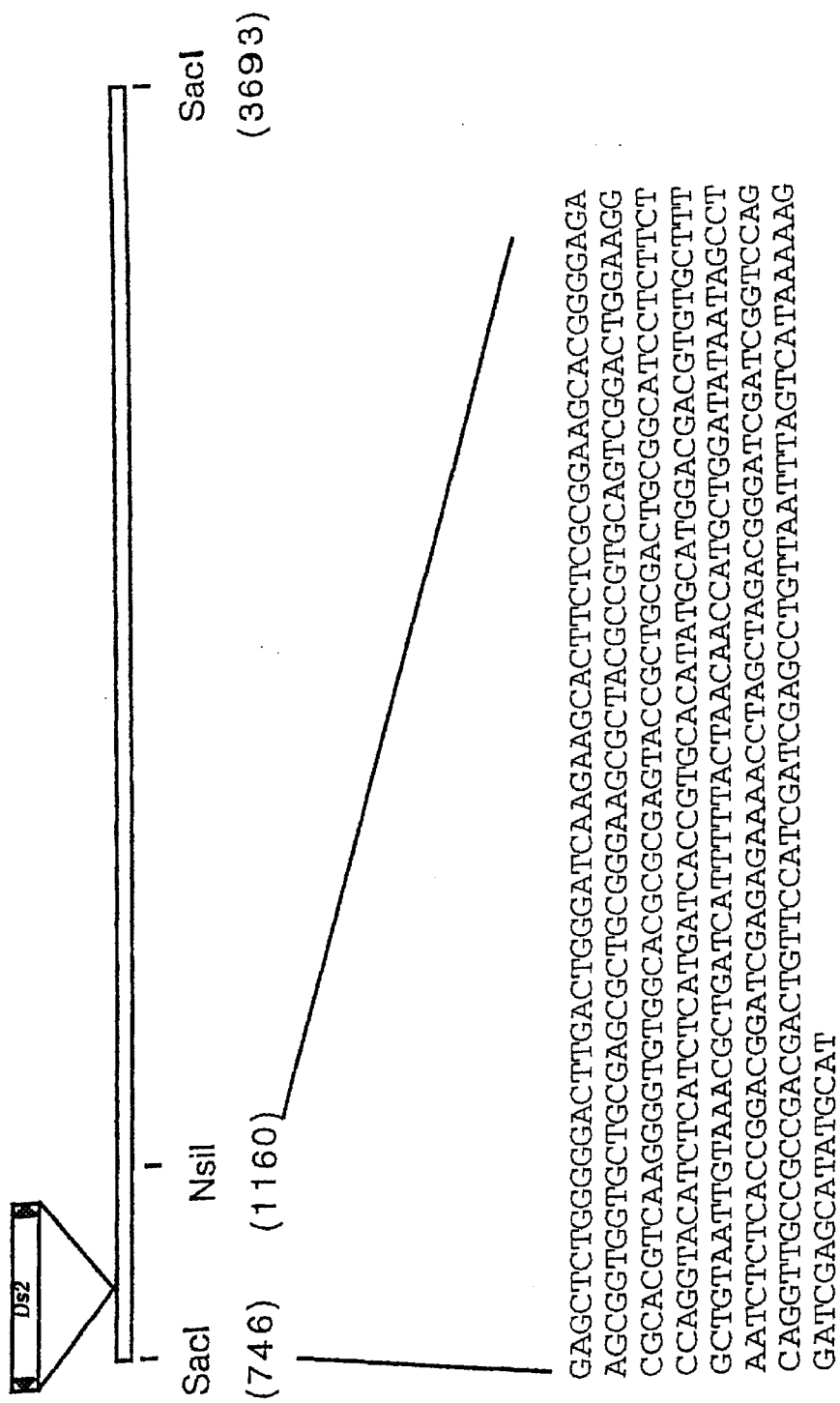
FIG. 4 is a restriction map of the conserved motif of the 4.2 kb SacI fragment which includes a portion of the Id gene. The location of the Ds2 transposon insertion and the genomic sequence (SEQUENCE ID NO:3) between restriction sites NsiI and SacI are shown.
Figure 5:
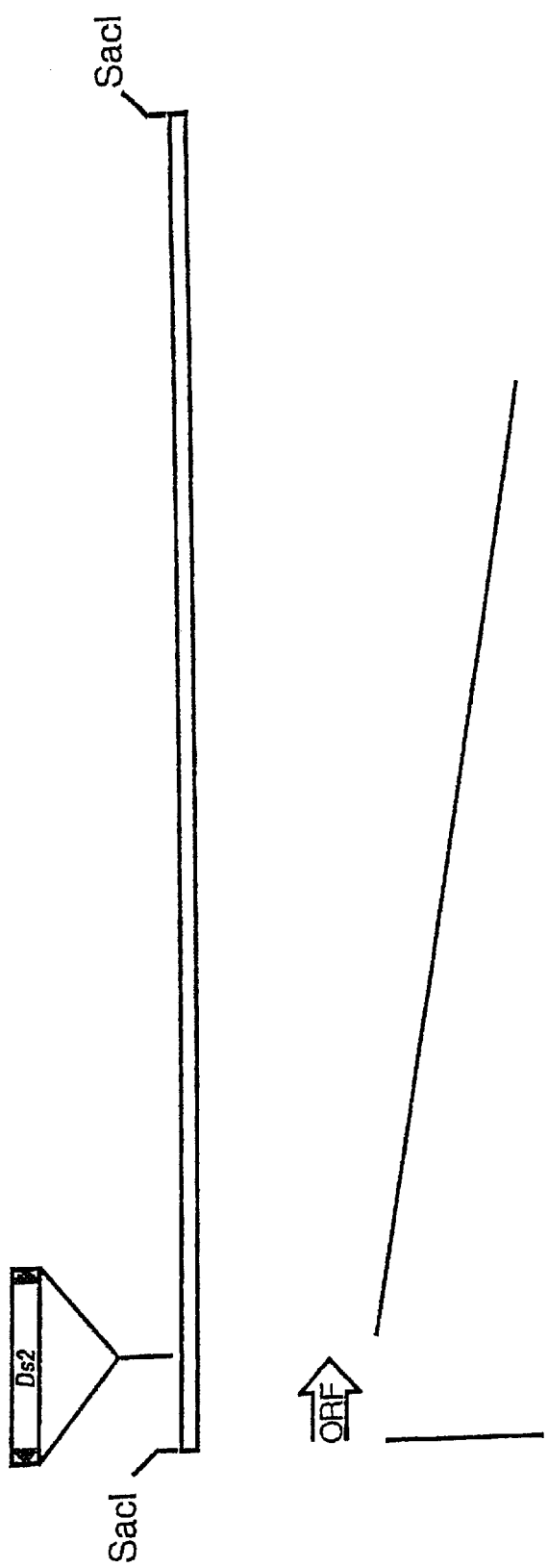
FIG. 5 shows the polypeptide sequence (SEQUENCE ID NO:4) encoded by SEQUENCE ID NO:3.

Southern blot analysis using the Ds2 element as a probe showed that a 4.2 kb SacI fragment co-segregates with the id* allele in more than 120 outcross progeny tested. This fragment is absent in plants that do not carry the id* allele. Cosegregation of this fragment with the id* allele is evidence that the gene is tagged with the Ds2 transposon. This fragment was isolated by separation of SacI cut genomic DNA on an agarose gel and excision of a region of the gel containing the fragment and sub-cloning into a plasmid vector to make a sub-library of genomic DNA in this region. The specific clone carrying the element was identified by probing the sub-library with the Ds2 probe. From 60,000 clones analyzed, one was found to contain the 4.2 kb SacI fragment. Restriction analysis showed that this recombinant clone carries a Ds2 fragment flanked by maize DNA: 165 bp of DNA to one side of the Ds2 element and 2.9 kb of DNA on the other side of the element (FIG. 4). Southern blots of DNA from various plants using either of the flanking regions as probes showed that plants that are homozygous for the id* allele contain a single SacI band of 4.2 kb whereas those that contain only normal DNA have a single 2.9 kb SacI fragment. Thus, the 4.2 kb fragment is the result of the insertion of the 1.3 kb Ds2 element into the 2.9 kb SacI fragment. Heterozygous plants contain both bands.

Further analysis of id* and other id mutants has demonstrated that these mutants are variations of the normal Id gene which generally result from insertion or deletion of a genetic element at different sites within the Id gene sequence, or deletion of all or a part of the Id gene itself. DNA from mutant plants carrying the first id allele to be identified, id-R, showed no hybridization to either of the flanking probes, indicating that this original allele is the result of a deletion of the Id gene. Another id allele, id-Compeigne, appears to have a 3 kb insertion into this fragment. These results provide convincing evidence that Applicants have tagged the id gene with Ds2.

Sequence analysis of the DNA immediately flanking the Ds2 element of the Id gene revealed an open reading frame (ORF) into which the transposon has been inserted (FIG. 4). When an RNA blot was probed with flanking DNA fragment that contained this ORF, a band of approximately 2.0–2.2 kb was evident in polyA+ RNA from apical meristem and, to a lesser extent, in mature leaf. An additional band of 1.6 kb was found in immature leaf. Very little hybridization was detected in seedling RNA and none was detected in RNA from roots. This indicates that the ORF encodes a transcript and that the transcript is differentially expressed in specific plant tissues.

A family of id-like genes that contains sequences very similar to this probe has been discovered. Therefore, the bands of 1.6 kb and of approximately 2.0–2.2 kb are hybridizing to all id-like genes, including Id. Another probe that has been discovered, which is specific for id, shows a band only in immature leaf tissue and is only of the size 1.6 kb.

Analysis of the deduced amino acid sequence encoded by the ORF provided further evidence that this ORF is part of the Id gene and that it plays an important role in plant development. A comparison of this ORF to all proteins in current databases shows that it has significant homology to "zinc-finger"-like proteins identified in many different eukaryotes, including humans, mice, frogs (Xenopus) and Drosophila (FIG. 6). Zinc-finger proteins are known as a class of diverse eukaryotic transcription factors that utilize zinc-containing DNA-binding domains and are important regulators of development. McKnight, S. L. and K. R. Yamamoto, eds. (1992) *Transcriptional Regulation.* Cold Spring Harbor Laboratory Press, Cold Spring Harbor, N.Y., Vol. 1, p. 580. Zinc-finger proteins exert a regulatory function by mediating the transcription of other genes.

Results described herein show that the Id gene is important in a crucial point in plant development (i.e., the transition from vegetative to reproductive growth) and that it functions by controlling the expression of other plant genes required for floral development. It is clearly a "switch" and nothing else in maize produces its effect (flower induction) without affecting the health and vigor of the plant. Conversely, mutation of Id alters or inhibits flower induction only; otherwise, the mutants are healthy and grow well.

Further evidence that the cloned DNA fragment is part of the Id gene was produced by generating five new alleles of id by imprecise excision of the Ds2 element from the original id* allele. Unlike id*, these new alleles no longer respond to Ac; they are null mutants that appear not to flower at all. Sequence analysis shows that four of the five alleles (id1-X1, id1-X2, id1-XD17 and id1-XD27) have an altered sequence which results in a frame shift in the Id open reading frame caused by the excision of Ds2 (FIG. 7), and therefore, do not encode the same polypeptide as the Id gene. The remaining allele (id1-XG9) results in the addition of a single serine residue in the id protein.

FIG. 7 illustrates the DNA and amino acid sequence of a portion of the normal Id ORF and its alteration as a consequence of Ds insertion and excision. The id-Ds mutation in id* which is produced by insertion of the Ds transposon shows the 8 bp target site duplication (underlined) which is typical of Ds insertion. The null mutants, id1-X1 and id1-X2, are stable, derivative alleles of id resulting from excision of Ds2. The id1-X1 allele has 7 bp of the duplication site remaining and an altered nucleotide (T to A). The id1-X2 allele has 5 bp of the duplication site remaining with the same T to A transition as id1-X1. The resulting amino acid residues show the frame shift in the ORF. The id1-XD17 allele, much like the id1-X1 allele, has 7 bp of the duplication site remaining and an altered nucleotide (T to A). The id1-XD27 allele has 4 bp of the duplication site remaining as a result of a bp deletion (4 bp from the duplication site and 6 bp from the region following the duplication site). The id1-XG9 allele has 3 bp of the duplication site remaining, which resulted in the addition of a single serine residue in the id protein. The id1-XG9 allele shows that alterations near the zinc finger region, even if only one amino acid, result in a major effect on id function. This effect is demonstrated by the increased number of leaves found on the id1-XG9 plant relative to the wild type plant and a long delay before flower evocation. The entire clone carrying the 4.2 kb SacI fragment was analyzed and the complete sequence of the genomic DNA flanking the Ds2 element (SEQ ID NO:1) determined (FIGS. 2A–2B) using the information provided herein and methods of analysis known to those of ordinary skill in the field. A sequence of 3669 nucleotides comprises DNA of the Id gene. The deduced amino acid sequence (SEQ ID NO:2) encoded by this DNA is shown in FIG. 3.

The nucleotide sequence of the Id gene has several features. Coding of the amino acid sequence begins with the start codon at nucleotide 12 and ends with the stop codon at nucleotide 2955 (FIGS. 2A and 2B). Two zinc-finger motifs are present: one consists of nucleotides 392–454 and the other consists of nucleotides 814–876. There are three introns consisting, respectively, of nucleotides 241–330, nucleotides 628–746, and nucleotides 921–2346. The polyadenylation site begins at nucleotide 3175. The ORF located between the NsiI and SacI restriction sites described supra (SEQ ID NO:3), is represented by nucleotides at positions 746–1160 in FIG. 3. The original SacI/SacI genomic fragment extends from nucleotides 746 to 3693.

The invention relates to methods using isolated and/or recombinant nucleic acids (DNA or RNA) that are characterized by (1) their ability to hybridize to (a) a nucleic acid encoding an Id protein or polypeptide, such as a nucleic acid having the sequence of SEQ ID NO:1 or (b) a portion of the foregoing (e.g., a portion comprising the minimum nucleotides required to encode a functional Id protein); or by (2) their ability to encode a polypeptide having the amino acid sequence of Id (e.g., SEQ ID NO:2), or to encode functional equivalents thereof; e.g., a polypeptide which when incorporated into a plant cell affects floral evocation in the same manner as Id (i.e., acts directly to signal floral induction); or by (3) both characteristics. A functional equivalent of Id, therefore, has a similar amino acid sequence and similar characteristics to, or performs in substantially the same way as, an Id protein. A nucleic acid which hybridizes to a nucleic acid encoding an Id polypeptide, such as SEQ ID NO:1, can be double- or single-stranded. Hybridization to DNA such as DNA having the sequence SEQ ID NO:1, includes hybridization to the strand shown or its complementary strand.

In one embodiment, the percent amino acid sequence similarity between an Id polypeptide such as SEQ ID NO:2 and functional equivalents thereof is at least about 80% (≧80%). In a preferred embodiment, the percent amino acid sequence similarity between a Id polypeptide and its functional equivalents is at least about 80% (≧80%). More preferably, the percent amino acid sequence similarity between an Id polypeptide and its functional equivalents is at least about 90%, and still more preferably, at least about 95%.

Isolated and/or recombinant nucleic acids meeting these criteria comprise nucleic acids having sequences identical to sequences of naturally occurring Id genes and portions thereof, or variants of the naturally occurring genes. Such variants include mutants differing by the addition, deletion or substitution of one or more nucleotides, altered or modified nucleic acids in which one or more nucleotides are modified (e.g., DNA or RNA analogs), and mutants comprising one or more modified nucleotides.

Such nucleic acids, including DNA or RNA, can be detected and isolated by hybridization under high stringency conditions or moderate stringency conditions, for example, which are chosen so as to not permit the hybridization of nucleic acids having non-complementary sequences. "Stringency conditions" for hybridizations is a term of art which refers to conditions such as temperature and buffer concentration which permit hybridization of a particular nucleic acid to another nucleic acid; the first nucleic acid may be completely complementary to the second, or the first and second may share some degree of complementarity which is less than complete. For example, certain high stringency conditions can be used which distinguish completely complementary nucleic acids from those of less complementarity. "High stringency conditions" and "moderate stringency conditions" for nucleic acid hybridizations are explained on pages 2.10.1–2.10.16 (see particularly 2.10.8–11) and pages 6.3.1–6 in *Current Protocols in Molecular Biology* (Ausubel, F. M. et al., eds., Vol. 1, containing supplements up through Supplement 29, 1995), the teachings of which are hereby incorporated by reference. The exact conditions which determine the stringency of hybridization depend not only on ionic strength, temperature and the concentration of destabilizing agents such as formamide, but also on factors such as the length of the nucleic acid sequence, base composition, percent mismatch between hybridizing sequences and the frequency of occurrence of subsets of that sequence within other non-identical sequences. Thus, high or moderate stringency conditions can be determined empirically.

High stringency hybridization procedures can (1) employ low ionic strength and high temperature for washing, such as 0.015 M NaCl/0.0015 M sodium citrate, pH 7.0 (0.1×SSC) with 0.1% sodium dodecyl sulfate (SDS) at 50° C.; (2) employ during hybridization 50% (vol/vol) formamide with 5×Denhardt's solution (0.1% weight/volume highly purified bovine serum albumin/0.1% wt/vol Ficoll/0.1% wt/vol polyvinylpyrrolidone), 50 mM sodium phosphate buffer at pH 6.5 and 5×SSC at 42° C.; or (3) employ hybridization with 50% formamide, 5×SSC, 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC and 0.1% SDS.

By varying hybridization conditions from a level of stringency at which no hybridization occurs to a level at which hybridization is first observed, conditions which will allow a given sequence to hybridize with the most similar sequences in the sample can be determined.

Exemplary conditions are described in Krause, M. H. and S. A. Aaronson (1991) *Methods in Enzymology*, 200:546–556. Also, see especially page 2.10.11 in *Current Protocols in Molecular Biology* (supra), which describes how to determine washing conditions for moderate or low stringency conditions. Washing is the step in which conditions are usually set so as to determine a minimum level of complementarity of the hybrids. Generally, from the lowest temperature at which only homologous hybridization occurs, a 1% mismatch between hybridizing nucleic acids results in a 1° C. decrease in the melting temperature $T_m$, for any chosen SSC concentration. Generally, doubling the concentration of SSC results in an increase in $T_m$ of ~17° C. Using these guidelines, the washing temperature can be determined empirically for moderate or low stringency, depending on the level of mismatch sought.

Isolated and/or recombinant nucleic acids that are characterized by their ability to hybridize to (a) a nucleic acid encoding an Id polypeptide, such as the nucleic acid depicted as SEQ ID NO:1, (b) the complement of SEQ ID NO:1, (c) or a portion of (a) or (b) (e.g. under high or moderate stringency conditions), may further encode a protein or polypeptide having at least one function characteristic of an Id polypeptide, such as floral evocation activity, or binding of antibodies that also bind to non-recombinant Id. The catalytic or binding function of a protein or polypeptide encoded by the hybridizing nucleic acid may be detected by standard enzymatic assays for activity or binding. Enzymatic assays, complementation tests, or other suitable methods can also be used in procedures for the identification and/or isolation of nucleic acids which encode a polypeptide such as a polypeptide of the amino acid sequence SEQ ID NO:2, or a functional equivalent of this polypeptide. The antigenic properties of proteins or polypeptides encoded by hybridizing nucleic acids can be determined by immunological methods employing antibodies which bind to an Id polypeptide such as immunoblot, immunoprecipitation and radioimmunoassay. PCR methodology, including RAGE (Rapid Amplification of Genomic DNA Ends), can also be used to screen for and detect the presence of nucleic acids which encode Id-like proteins and polypeptides, and to assist in cloning such nucleic acids from genomic DNA. PCR methods for these purposes can be found in Innis, M. A., et al. (1990) *PCR Protocols: A Guide to Methods and Applications*, Academic Press, Inc., San Diego, Calif., incorporated herein by reference.

The nucleic acids described herein are used in the methods of the present invention for production of proteins or polypeptides which are incorporated into plant cells and which directly affect floral evocation in plants. In one embodiment, DNA containing all or part of the coding sequence for an Id polypeptide, or DNA which hybridizes to DNA having the sequence SEQ ID NO:1, is incorporated into a vector for expression of the encoded polypeptide in suitable host cells. A vector, therefore, includes a plasmid or viral DNA molecule into which another DNA molecule can be inserted without disruption of the ability of the molecule to replicate itself.

Nucleic acids referred to herein as "isolated" are nucleic acids separated away from the nucleic acids of the genomic DNA or cellular RNA of their source of origin (e.g., as it exists in cells or in a mixture of nucleic acids such as a library), and may have undergone further processing. "Isolated" nucleic acids include nucleic acids obtained by methods described herein, similar methods or other suitable methods, including essentially pure nucleic acids, nucleic acids produced by chemical synthesis, by combinations of biological and chemical methods, and recombinant nucleic acids which are isolated. Nucleic acids referred to herein as "recombinant" are nucleic acids which have been produced by recombinant DNA methodology, including those nucleic acids that are generated by procedures which rely upon a method of artificial recombination, such as the polymerase chain reaction (PCR) and/or cloning into a vector using restriction enzymes. "Recombinant" nucleic acids are also those that result from recombination events that occur through the natural mechanisms of cells, but are selected for after the introduction to the cells of nucleic acids designed to allow or make probable a desired recombination event. Portions of the isolated nucleic acids which code for polypeptides having a certain function can be identified and isolated by, for example, the method of Jasin, M., et al., U.S. Pat. No. 4,952,501.

A further embodiment of the invention is antisense nucleic acids or oligonucleotides which are complementary, in whole or in part, to a target molecule comprising a sense strand, and can hybridize with the target molecule. The target can be DNA, or its RNA counterpart (i.e., wherein T residues of the DNA are U residues in the RNA counterpart). When introduced into a cell, antisense nucleic acids or oligonucleotides can inhibit the expression of the gene encoded by the sense strand or the mRNA transcribed from the sense strand. Antisense nucleic acids can be produced by standard techniques. See, for example, Shewmaker, et al., U.S. Pat. No. 5,107,065.

In a particular embodiment, an antisense nucleic acid or oligonucleotide is wholly or partially complementary to and can hybridize with a target nucleic acid (either DNA or RNA), wherein the target nucleic acid can hybridize to a nucleic acid having the sequence of the complement of the strand in SEQ ID NO:1. For example, an antisense nucleic acid or oligonucleotide can be complementary to a target nucleic acid having the sequence shown as the strand of the open reading frame, complementary to nucleotides 380–442, or complementary to nucleotides 796–858 of SEQ ID NO:1, or nucleic acid encoding a functional equivalent of Id, or to a portion of these nucleic acids sufficient to allow hybridization. A portion, for example, a sequence of 16 nucleotides, could be sufficient to inhibit expression of the protein. In another embodiment, the antisense nucleic acid is wholly or partially complementary to and can hybridize with a target nucleic acid which encodes an Id polypeptide.

The invention also relates to methods using the proteins or polypeptides encoded by nucleic acids of the present invention. The proteins and polypeptides of the present invention can be isolated and/or recombinant. Proteins or polypeptides referred to herein as "isolated" are proteins or polypeptides purified to a state beyond that in which they exist in cells. "Isolated" proteins or polypeptides include proteins or polypeptides obtained by methods described herein, similar methods or other suitable methods, and include essentially pure proteins or polypeptides, proteins or polypeptides produced by chemical synthesis or by combinations of biological and chemical methods, and recombinant proteins or polypeptides which are isolated. Proteins or polypeptides referred to herein as "substantially purified" have been isolated and purified, such as by one or more steps usually including column chromatography, differential precipitation, or the like, to a state which is at least about 10% pure. Proteins or polypeptides referred to herein as "recombinant" are proteins or polypeptides produced by the expression of recombinant nucleic acids.

The reproductive capacity of a plant directly affects its ability to yield seeds. Therefore, the ability to control flowering time is an important factor in the life cycle of the plant. The genetic studies of the id mutation of maize described herein indicate that the Id gene encodes a protein that is required for the transition to flowering. Through the use of transposon tagging, the Applicants have isolated and characterized the Id gene and, in particular, a portion of the zinc-finger regulatory regions of this gene. Further, molecular analysis and comparison to eukaryotic animal regulatory proteins shows that the polypeptide encoded by this region is part of, if not the major component of, the regulatory Id protein that controls flower initiation and, very likely, also controls transition to reproduction from the vegetative growth stage of gymnosperms and lower plants, including the algae.

The DNA provided by this invention can be used to isolate homologous or analogous nucleic acids from other species of plants which encode regulatory genes for flowering similar in function to the Id gene. In the context of this invention, the term "homology" means an overall sequence identity of at least 50%, preferably 70% or more for the zinc-finger portions of the Id allele. The identification and isolation of Id-type genes (homologues of Id) of other plant species is carried out according to standard methods and procedures known to those of ordinary skill in the art. See, e.g., Sambrook, et al. (1989) *Molecular Cloning—A Laboratory Manual*, Cold Spring Harbor Laboratory Press, Cold Spring Harbor, N.Y. An example of this application is found in Example 5, infra.

By using these and other similar techniques, those of ordinary skill can readily isolate not only the Id gene in different cells and tissues of maize, but also homologues of the Id allele from other plant species. By example, Id genes in plants can be identified by preparing a genomic or cDNA library of a plant species; probing the genomic or cDNA library with all or a portion or a homologue of SEQ ID NO:1; identifying the hybridized sequences; and isolating the hybridized DNA to obtain the Id gene of that plant. Once identified, these genes can be restriction mapped, sequenced and cloned. In particular, the zinc-finger regions or fragments thereof are especially effective as probes because of their conserved homology to other zinc-finger regions.

Other zinc-finger proteins that regulate phenomena other than flower initiation may be present in maize and other plants. Regulatory genes may control the germination of seeds, the height and shape of plants, the number of leaves, and the ripening of fruits to name a few possibilities. The isolation and characterization of these genes as well as the genes responsible for initiation of the reproductive phase in plants would be of great significance and value in flower, food, and crop production in general. Such zinc-finger genes in plants can be identified by preparing a genomic or a cDNA library of a plant species; probing the genomic or cDNA library with all or a portion or a homologue of the Id gene, described herein, such as SEQ ID NO:1, under conditions appropriate for hybridization of complementary DNA identifying the hybridized DNA; and isolating the hybridized DNA to obtain the zinc-finger gene in that plant. The zinc-finger genes can then be restriction mapped, sequenced and cloned.

This invention also provides nucleic acids and polypeptides with structures that have been altered by different means, including but not limited to, alterations using transposons, site-specific and random mutagenesis, and engineered nucleotide substitution, deletion, or addition.

A transposon method of producing an allele of the Id gene with an altered function in a plant can comprise: inserting the Ds transposon or another nonautonomous transposable element into the Id gene, and then excising the Ds transposon with the Ac transposon or another autonomous transposable element to produce an altered Id allele in the plant.

A further example of a method of producing an allele of the Id gene with an altered function in a plant comprises altering the molecular structure of the Id gene in vitro using molecular genetic techniques (e.g., site specific mutagenesis), and then inserting the altered Id gene into a plant to produce an altered Id allele in the plant.

These techniques can give rise to Id homologs which demonstrate dramatically different functions from the corresponding naturally-occurring protein. For example, site-directed mutagenesis can be used to produce Id alleles that encode specific substitutions of amino acid residues and it can then be determined what amino acids are required to produce a functional gene, the product of which induces a reproductive response in plants. Likewise, Id alleles can be engineered to produce proteins that have novel functions, such as flower induction earlier than that of the naturally-occurring plant.

There are many varieties of maize that have evolved a wide range of flowering times depending on the environmental conditions in which they are grown. In particular, day-length (as dictated by latitude) determines when a plant will flower. The Id gene is a determinant of flowering time in all of these maize variants, and flowering time may be correlated to specific variations in the Id gene product. In fact, the Id gene may be the major determinant of floral evocation.

The Id gene or a homologue thereof can be altered and introduced into a maize plant to alter the flowering time of a particular type of maize so that it can be grown in a different latitude from the one in which the parent strain was developed. Thus, an engineered Id gene can be incorporated into a maize line that has been bred for other traits (e.g., high yield and disease resistance), to produce a maize line that can be grown at many different latitudes. Lowering the level of Id protein using antisense constructs or co-suppression (see below) can delay flowering time, while increasing the level of Id by overexpression or through earlier production (Id gene coupled to a different promoter) of the protein can induce plants to flower sooner. Further, putting the sense or antisense Id gene under the control of different inducible promoters can permit flowering time to be controlled when subjected to specific environmental conditions or to applied chemicals.

Co-suppression refers to the overexpression of an endogenous or an introduced gene (transgene) wherein the extra copies of the gene result in the coordinate silencing of the endogenous gene as well as the transgene, thus reducing or eliminating expression of the trait. See, for example, Jorgensen et al., U.S. Pat. Nos. 5,034,323 and No. 5,283,184. The transgene is introduced in a sense orientation and does not require a full length sequence or absolute homology to the endogenous sequence intended to be repressed.

Expression of the endogenous gene may also be suppressed through the integration of an oligonucleotide having an identical or homologous sequence to that of the DNA strand complementary to the strand transcribing the endogenous gene. Antisense oligonucleotides comprise a specific sequence of nucleotide residues that provide an RNA which stably binds to the RNA transcribed from the endogenous gene, thus preventing translation. See, Shewmaker et al., U.S. Pat. No. 5,107,065.

Other oligonucleotides of this invention called "ribozymes" can be used to inhibit or prevent flowering. Unlike antisense and other oligonucleotides which bind to an RNA, a DNA, or a protein, ribozymes are catalytic RNA molecules which can bind and specifically cleave a target RNA, such as the transcription product of an endogenous Id gene. Ribozymes designed to cleave at specific sites can inactivate such an RNA molecule. Thus reduction of an Id product can be achieved by introduction of DNA which encodes a ribozyme designed to specifically cleave transcripts of endogenous Id genes in an endonucleolytic manner.

Of the known classes of ribozymes, the group I intron and hammerhead ribozymes are useful candidates to convert for targeted cleavage of an Id transcript since they have short (4–12 base) recognition sequences; however, other types of ribozymes can be developed for site-specific cleavage of Id mRNA. See, Cech, T. R. (1988) *J. Amer. Med. Assoc.* 260:3030–3034.

The above strategies to delay or completely abolish flowering depend upon the use of antisense and similar technologies. An alternative strategy can be devised based upon the use of "dominant-negative" mutant proteins. Certain types of mutations can be introduced into regulatory proteins that render them non-functional, but permit the mutant proteins to compete with the wild type proteins for their targets. Such competition by a non-functional protein means that overexpression of the mutant protein can be used to suppress the activity of the wild type protein. Dominant-negative mutations of zinc-finger transcription factors have been constructed in fruit-flies and in human cells by deleting the activation/silencer domain while retaining the DNA-binding zinc-finger domain. The over-expressed mutant protein then competes out the wild type protein by binding non-productively to the DNA targets. O'Neill, E. M. et al. (1995) *Proc. Nat'l. Acad. Sci. USA* 92: 6557–6561. In plants, dominant-negative strategies have been used successfully with other types of regulatory proteins. See, Boylan, M. et al. (1994) *Plant Cell* 6: 449–460; Rieping, M. et al. (1994) *Plant Cell* 6: 1087–1098; and Hemerly, A. et al. (1995) *EMBO J.* 14: 3925–3936.

A dominant-negative mutant of the Id protein can be constructed by using a truncated version of the Id gene that contains only the sequences encoding the zinc-finger domains (the presumptive DNA-binding domains), and is missing the activation domain. If this truncated gene is introduced into maize plants under the control of a strong promoter, the result will be maize plants that are either severely delayed in flowering or are unable to flower. Therefore, the truncated dominant-negative Id gene can be substituted for the antisense Id gene in all of the constructs used to delay flowering herewith described.

The dominant-negative Id gene approach has an advantage over the antisense construct when engineering delayed flowering into crops other than maize. The antisense strategy depends on initially cloning part or all of the Id gene from each crop species, then expressing these genes in an inverted orientation. Antisense suppression depends on expression of the complementary nucleotide sequences, which will vary from one crop species to another. In contrast, the dominant-negative strategy depends only upon the functional conservation of the protein and its target sites. Overall, this is a much less stringent requirement than nucleotide sequence conservation. Several known examples of regulatory genes encoding transcription factors perform similar functions when expressed in widely divergent species of plants. See, e.g., Lloyd, A. M. et al. (1992) *Science* 258: 1773–1775; Irish, V. F. and Y. T. Yamamoto (1995) *Plant Cell* 7:1635–1644. This type of functional conservation implies that the dominant-negative version of the maize Id gene can work similarly in other crop species as well. It can certainly be expected to function in other cereal species and perhaps in all monocotyledonous plants.

For application to dicots, it could be advantageous to first isolate a more closely-related Id homolog from a dicotyledonous species (e.g., tobacco or Arabidopsis), and construct a dominant-negative derivative as described above (by removing all sequences other than the zinc-finger DNA binding domains). This dicot version of dominant-negative Id can then be used for all dicot plants. Thus, application of dominant-negative technology to a wide range of crops can be achieved without the need to clone Id genes from every crop.

Any suitable technique can be used to introduce the nucleic acids and constructs of this invention to produce transgenic plants with an altered floral induction time. For grasses such as maize, microprojectile bombardment (see for example, Sanford, J. C., et al., U.S. Pat. No. 5,100,792 (1992) can be used. In this embodiment, a nucleotide construct or a vector containing the construct is coated onto small particles which are then introduced into the targeted tissue (cells) via high velocity ballistic penetration. The vector can be any vector which expresses the exogenous DNA in plant cells into which the vector is introduced. The transformed cells are then cultivated under conditions appropriate for the regeneration of plants, resulting in production of transgenic plants. Transgenic plants carrying the construct are examined for the desired phenotype using a variety of methods including but not limited to an appropriate phenotypic marker, such as antibiotic resistance or herbicide resistance, or visual observation of the time of floral induction compared to naturally-occurring plants.

Other known methods include Agrobacterium-mediated transformation (see for example Smith, R. H., et al., U.S. Pat. No. 5,164,310 (1992)), electroporation (see for example, Calvin, N., U.S. Pat. No. 5,098,843 (1992)), introduction using laser beams (see for example, Kasuya, T., et al., U.S. Pat. No. 5,013,660 (1991)) or introduction using agents such as polyethylene glycol (see for example Golds, T., et al. (1993) *Biotechnology*, 11:95–97), and the like. In general, plant cells may be transformed with a variety of vectors, such as viral, episomal vectors, Ti plasmid vectors and the like, in accordance with well known procedures. The method of introduction of the nucleic acid into the plant cell is not critical to this invention.

The transcriptional initiation region may provide for constitutive expression or regulated expression. Many promoters are available which are functional in plants. Illustrative promoters include the octopine synthase promoter, the nopaline synthase promoter, the cauliflower mosaic virus (35S) promoter, the figwort mosaic virus (FMV) promoter, heat-shock promoters, ribulose-1,6-biphosphate (RUBP) carboxylase small subunit (ssu), tissue specific promoters, and the like. The regulatory region may be responsive to a physical stimulus, such as light, as with the RUBP carboxylase ssu, differentiation signals, or metabolites. The time and level of expression of the sense or antisense orientation can have a definite effect on the phenotype produced. Therefore, the promoters chosen, coupled with the orientation of the exogenous DNA, will determine the effect of the introduced gene.

Transgenic plants of this invention can contain an exogenous nucleic acid which alters the time of floral induction so that floral induction is earlier than that of a plant of the same variety without said exogenous nucleic acid when grown under identical conditions. Alternatively, transgenic plants containing an exogenous nucleic acid which alters the time of floral induction so that floral induction is delayed or inhibited compared to floral induction in a plant of the same variety without said exogenous nucleic acids when grown under identical conditions.

Further, this invention includes a method of producing a transgenic plant having an altered time of flower induction, comprising introducing into plant cells an exogenous nucleic acid whose presence in a plant results in altered time of induction of flower development, and maintaining plant cells containing the exogenous nucleic acid under conditions appropriate for growth of the plant cells, whereby a plant having an altered reproduction induction time is produced. Organisms to which this method can be applied include: angiosperms (monocots and dicots), gymnosperms, spore-bearing or vegetatively-reproducing plants and the algae.

Transgenic plants containing the Id recombinant constructs can be regenerated from transformed cells, tissues or plant parts by methods known to those of skill in the art. Plant part is meant to include any portion of a plant capable of producing a regenerated plant. Thus, this invention encompasses a cell or cells, tissue (especially meristematic and/or embryonic tissue), protoplasts, epicotyls, hypocotyls, cotyledons, cotyledonary nodes, pollen, ovules, stems, roots, leaves, and the like. Plants may also be regenerated from explants. Methods will vary according to the plant species.

Seed can be obtained from the regenerated plant or from a cross between the regenerated plant and a suitable plant of the same species. Alternatively, the plant may be vegetatively propagated by culturing plant parts under conditions suitable for the regeneration of such plant parts.

Isolated and purified Id or id protein or polypeptides, and epitopic fragments thereof, can be used to prepare antibodies for localization of sites of Id regulation and to analyze developmental pathways in plants. For example, antibodies that specifically bind an Id protein can be used to determine if and when the protein is expressed in specific cells or tissues of the plant. This information can be used to determine how Id acts to induce flowering and to alter flower induction pathways.

Antibodies of the invention can be polyclonal, monoclonal, or antibody fragments, and the term antibody is intended to encompass polyclonal antibodies, monoclonal antibodies and antibody fragments. Antibodies of this invention can be raised against isolated or recombinant Id or id proteins or polypeptides. Preparation of immunizing antigen, and antibody production can be performed using any suitable technique. A variety of methods have been described (see e.g., Harlow, E. and D. Lane (1988) *Antibodies: A Laboratory Manual*, Cold Spring Harbor Laboratory Press, Cold Spring Harbor, N.Y.; Ausubel et al. (1994) *Current Protocols in Molecular Biology*, Vol. 2, Chapter 11 (Suppl. 27) John Wiley & Sons: New York, N.Y.).

Antibodies of this invention can be labeled or a second antibody that binds to the first antibody can be labeled by some physical or chemical means. The label may be an enzyme which is assayed by the addition of a substrate which upon reaction releases an ultraviolet or visible light-absorbing product or it can be a radioactive substance, a chromophore, or a fluorochrome. E. Harlow and D. Lane (1988) supra.

Isolated polypeptides of this invention can also be used to detect and analyze protein/protein interactions. Fusion proteins for this purpose can be prepared by fusing Id DNA encoding a functional Id polypeptide with heterologous DNA encoding a different polypeptide (one not related or homologous to the Id polypeptide), such as a protein tag. The resulting fusion protein can be prepared in a prokaryotic cell (e.g. *E. coli*), isolated, labeled and used essentially like antibodies to detect binding sites of Id alleles and Id/protein interactions. See Ron and Dressler (1992) *Biotech* 13:866–69; Smith and Johnson (1988) *Gene* 67:31–40.

Figure 8A:
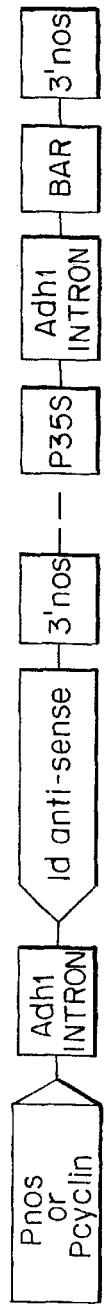
FIGS. 8A–8B depict schematic representations of Id antisense constructs in which a weak promoter is fused with the Id cDNA for production of transgenic (FIG. 8A) monocots or (FIG. 8B) dicots to delay flowering in an early flowering line.

Maize lines that are adapted to temperate latitudes flower prematurely when planted in the tropics due to the shorter daylengths. The premature flowering results in severely reduced yields. Salamini, F. (1985) *Breeding Strategies for Maize Production Improvement in the Tropics*. Brandolini, A. and Salamini, F., eds. Food and Agriculture Organization of U.N., Istituto Agronomico Per L'Oltremare, Firenze, Italy. One of skill in the art will recognize that the cloned Id gene can be used to overcome this problem. Transgenic maize plants can be generated in which the Id gene is inserted in the antisense orientation under the control of a weak promoter (FIG. 8A). The weak promoter used should be constitutively active during development, at least in the shoot meristem. Since Id appears to be non cell-autonomous, exact specification of the site of action of the promoter is not necessary. An example of a weak promoter useful for this application is the nopaline synthase (nos) promoter, from T-DNA, shown to be weakly constitutive in maize. Callis, et al. (1987) *Genes Dev.* 1:1183–1200. Another is a cyclin promoter from maize. Cyclins are cell division proteins found in plants, animals and yeasts. Plant cyclin transcripts are expressed in meristems and tissues with proliferating cells at low levels, but are not expressed elsewhere. Renaudin, et al. (1994) *PNAS* 91:7375–7379. The cyclin promoters are easily isolated by using Applicants' full-length cDNA clones for cyclin 1b or cyclin III as probes, to pull out the flanking upstream genomic sequences from a maize genomic library using standard isolation and cloning techniques. See, Sambrook, et al., supra; Freeling and Walbot, supra. Those skilled in the art will recognize the other weak promoters intended to be encompassed by the invention that have the characteristics necessary to carry out this embodiment of the invention.

An example of a construct useful for the above application is illustrated in FIG. 8A. The cDNA for the Id gene is ligated downstream from the promoter, in the antisense orientation. The ADH1 intron is required for RNA stability, and the 3' end of the nos gene is added to ensure efficient polyadenylation. Callis, et al. (1987) supra. The DNA is introduced into maize plants by standard methods such as those described above, using the bar gene for resistance to the herbicide Basta as the transformation marker. Gordon-Kamm, et al. (1990) *Plant Cell* 2:603–618; Freeling and Walbot (1993) supra.

Any construct or vector which expresses the exogenous DNA in plant cells into which it is introduced can be used, such as the pMON530 vector carrying the 35S promoter. Another useful vector or construct of the present invention is exogenous DNA encoding the id protein inserted in the antisense orientation into the pMON530 vector downstream of a weak promoter to delay flowering in an early-flowering variety.

Similar constructs can he used for other cereals, e.g., rice, barley, and other monocotyledonous crops. For antisense applications, it may be necessary to first isolate the homologous cDNA from the species to be modified. It will be recognized that the maize Id clone can be used as a probe for this purpose, screening for Id homologues from cDNA libraries of the other cereal species. The Id homologue for the species to be engineered can then be inserted as a substitution for the maize Id gene in the constructs of FIG. 8A.

Figure 8B:
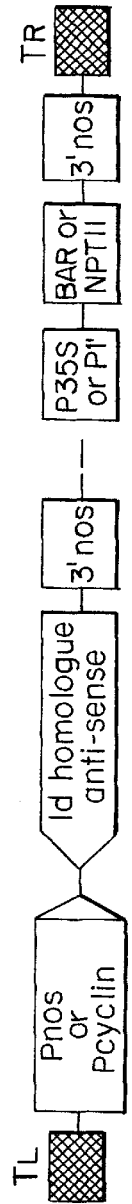

The same technique can be extended to dicotyledonous plants as well. Delaying flowering time for some of these crops can result in advantages similar to those cited for maize, i.e., a longer vegetative growth period that results in higher yields of fruits and seeds. Gottschalk and Wolff (1983) *Induced Mutations in Plant Breeding*, Springer-Verlag, Berlin, Heidelberg. In addition, some dicotyledonous plants are valuable chiefly for the products of vegetative growth (e.g., spinach, tobacco, etc.), and, in these plants, extended vegetative growth will result in higher and more efficient yields of products. Antisense constructs can be designed using Id homologues isolated from these species, as shown in FIG. 8B, and transgenic plants generated by T-DNA transformation, preferably using Agrobacterium transformation techniques, but also by other standard techniques. Lycett, G. W. and D. Grierson (1990) *Genetic Engineering of Crop Plants*, Butterworths, London; Setlow, J. K. (1994) *Genetic Engineering Principles and Methods*, Vol. 16, Plenum Press, New York.

Figure 9A:
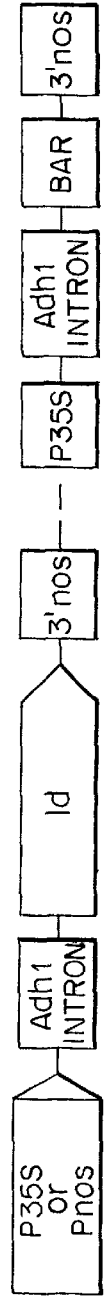
FIGS. 9A–9B depict schematic representations of Id sense construct in which a constitutive promoter is fused with the Id cDNA for production of transgenic (FIG. 9A) monocots or (FIG. 9B) dicots to induce early flowering in a late flowering line.

Maize varieties that are adapted to tropical latitudes flower extremely late when grown in temperate latitudes (Salamini, supra), reaching heights of 15–20 feet, with 30 leaves at flowering (compared to about 20 leaves on the average temperate variety). This is not only inconvenient for handling and harvesting, but makes the plants vulnerable to late season frost damage. A strategy to induce earlier flowering in these plants is to express the cloned Id gene early in the vegetative development of these varieties by inserting the gene in the sense orientation under a constitutive promoter (FIG. 9A). A strong or weak promoter can be used, such as the CaMV 35S (strong) promoter or the nos (weak) promoter, both of which function in maize. Callis, et al. (1987) supra. The constructs and transformation methods for this purpose are similar to those used in the antisense application described above, except for the orientation of the Id gene.

It will be recognized that this technique can be adapted for other cereal species and for monocots, in general, using the same constructs or constructs that are similar in principle. In fact, homologues of Id may not be required for early expression because a maize Id gene product could function adequately in other monocotyledons, including cereals, to promote earlier flowering.

Figure 9B:
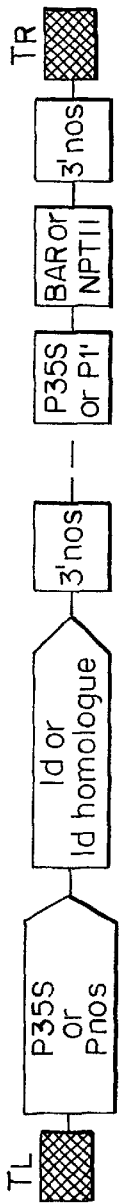

In another embodiment of this invention, earlier flowering of dicotyledonous plants can be provided by transforming target plants or plant cells with the maize Id gene product or an Id homologue. Because maize genes have been demonstrated to function efficiently in dicots, it may not be necessary to isolate the homologous gene from the species to be transformed. For example, the maize R and C genes function in the dicot Arabidopsis when expressed under control of the CaMV 35S promoter. Lloyd, et al. (1992) *Science* 258:1773–1775. The construct delineated in FIG. 9B can be used for expression of an Id gene or homologue in a dicot, and can be inserted with T-DNA transformation or other standard techniques such as those already described.

Drought stress can cause severe reduction in yields due to damage to the plant. In addition, the flowering time can be affected. Many plants flower prematurely when stressed. In maize, drought stress can result in the tassel developing much earlier than the ear, resulting in reduced yields or no yields. Some of these problems can be alleviated if the overall flowering time of the plant was delayed during a period of drought. This delay would allow the plant to grow vegetatively for a longer period of time than normal, so that it can recover from drought damage before it flowers. The Id gene can be used for this purpose, if it is introduced into the plants in the antisense orientation as described earlier, but combined with a drought-inducible promoter instead of a constitutive promoter. Any drought-inducible promoter can be used. For example, a promoter for the RAB-17 gene, which is induced by drought as well as other stresses, presumably as a result of its regulation by the plant hormone ABA can be used. Vilardell, et al. (1990) *Plant Mol. Biol.* 14:423–432. A second type of promoter which can be used is the maize hsp70 heat shock promoter, which is induced in response to high temperatures 37° to 42° C. Callis, et al. (1988) *Plant Physiol.* 88:965–968.

A useful vector or construct to produce plants responsive to environmental effects is produced by inserting the exogenous DNA encoding the Id protein in the antisense direction into the pMON530 vector downstream of a drought-induced promoter to delay flowering in response to drought. Several constructs for this purpose are illustrated in FIG. 10A.

Again, this technique can be extended to monocots in general, including other cereals, with the same constructs as in FIG. 10A or a similar construct, but using the homologue of the Id gene for the particular cereal being transformed if necessary.

The extension of this technique to dicotyledonous crops can be performed using appropriate drought inducible promoters that function in dicotyledonous plants. The promoter of the Arabidopsis Atmyb2 can be used as a general ABA-responsive, drought and stress-induced promoter. Urao, et al. (1993) *Plant Cell* 5:1529–1539. The soybean heat-shock promoter can also be used. Schoffl, et al. (1989) *Mol. Gen. Genet.* 217:246–253. Constructs including such promoters are illustrated in FIG. 10B. Since this application depends upon antisense expression, it may be necessary to use the homologue of the Id gene from the crop species that is being engineered, rather than the maize Id gene.

Of particular use are maize plants in which flowering is completely absent; i.e., knocked out. Maize plants that do not flower will continue to grow vegetatively, producing a large biomass which can be harvested for silage purposes. However, if the Id gene is knocked out completely for the purposes of producing silage, the transgenic plants will never flower and no hybrid seeds can be produced.

One method of this invention for generating hybrid seeds of transgenic corn is to produce transgenic plants with the Id gene in the antisense orientation, but under the control of a regulatory sequence called the GAL4 binding site. As a consequence, the antisense Id gene is not expressed unless the GAL4 protein is present. GAL4 is a transcription factor from yeast, which has been demonstrated to work in plants such as tobacco (Ma, J., et al. (1988) *Nature* 334:631–633), as well as in corn (McCarty, D. et al. (1991) *Cell* 66:895–905. It activates transcription of genes which contain the GAL4 binding site in the promoter.

In this embodiment, a transgenic inbred containing the silent antisense Id gene and the GAL4 binding site is crossed to another transgenic inbred which expresses the GAL4 gene constitutively, either under a weak promoter (to delay flowering for growth of corn in lower latitudes), or under a strong promoter (to abolish flowering for silage production). Each inbred flowers normally. However, the hybrid expresses the antisense Id, and flowering is delayed or absent, depending upon the promoter used to drive the GAL4 gene. A similar modification can be made for other plants, either monocots or dicots, using the appropriate Id homolog.

Constructs using the GAL4 binding site are illustrated in FIGS. 11A, 11B, 11C and 11D. Thus, in maize, an inbred comprising the construct illustrated in FIG. 11A is crossed with an inbred comprising the construct of FIG. 11C. Flowering is delayed in the resulting hybrid when the GAL4 gene is under the control of CaMV 35S (P35s). When the GAL4 gene is under the control of the nos (Pnos) or cyclin (Pcyclin) promoters, however, flowering is only delayed in the hybrid. In dicots, similar results are obtained by crossing the plant comprising the construct shown in FIG. 11C to the plant comprising the construct shown in FIG. 11D.

The applications described above illustrate the use of antisense Id constructs. It will be recognized by those of skill in the art that any suitable construct, for example, the dominant-negative version of the Id gene, can be substituted for the antisense constructs to practice the methods of this invention.

Although the Id gene was isolated from maize, it is likely that homologues of Id exist in other grain crops, and most likely in all other plants. Applicants have initial evidence that a close relative of Id, as determined by sequence homology, exists in dicotyledonous plants as well. If these homologues in other species are also important to the control of flowering time, then the manipulation of flowering time of many agriculturally important crops would be possible. Using the compositions and methods described herein, a skilled artisan can use known procedures to alter initiation of the reproductive phase of other grains such as sorghum, rye, wheat, etc., as well as in other commercially important plants.

For example, modifications of flowering time can be used to affect the time of ripening of fruit, time of production of flowers, size and quality of seed, latitude at which varieties can be grown, and the like. Flowering time may be modulated so that flowering is initiated at different times on different parts of the same plant.

This invention also provides a means to eliminate the need for detasseling in the production of maize and sorghum hybrids. Although it appears that Id does not act in a cell autonomous manner, it may be that the Id signal is localized to certain areas of the plant and thus Id must be transcribed or Id mRNA activated in several areas of the plant to induce flower development in each of these areas. Corn and sorghum both produce male flower organs (tassels) at the top (apex) of the plant. Female flower organs are produced on lower portions in the axils. Through the use of tissue-specific or other selective promoters coupled to the Id gene, it is possible to inhibit or prevent the production of pollen in the apex of the plant while selectively inducing reproductive development of the female reproductive organs on other parts of the plant. Or, after normal flower induction, development of male reproductive organs can be inhibited or pollen-producing tissues or cells can be induced to revert to vegetative phase by coupling Id antisense production to the formation of cells specific to pollen production (such as tapetal cells).

Another application of this technology is to increase the vegetative phase (and therefore increase the number of leaves produced) of crops that are harvested as leaves (e.g., lettuce, cabbage, spinach, maize) and thereby increase yield of these crops by delaying flowering. In still another application, where flowering produces an undesirable aesthetic appearance, the vegetative phase of a plant, e.g. turfgrass, can be prolonged. Thus, any plant may be employed in accordance with this invention, including angiosperms, gymnosperms, monocotyledons, and dicotyledons. Plants of interest include cereals such as wheat, barley, maize, sorghum, triticale, etc.; other commercially-valuable crops, such as sunflower, soybeans, safflower, canola, etc.; fruits, such as apricots, oranges, apples, avocados, etc; vegetables, such as carrots, lettuce, tomatoes, broccoli, etc; woody species, such as poplar, pine, oak, etc; and ornamental flowers, such as clematis, roses, chrysanthemums, tulips, etc.

The following examples describe specific aspects of the invention to illustrate the invention and provide a description of the methods used to isolate and identify the Id gene. The examples should not be construed as limiting the invention in any way.

All citations in this application to materials and methods are hereby incorporated by reference.

EXAMPLE 1

TRANSPOSON TAGGING:

Plants were grown under normal field conditions at Uplands Farm Agricultural Field Station, Cold Spring Harbor Laboratory, during the summers of 1989 through 1994. Standard maize genetic techniques were used in all crosses and analytical procedures. Freeling, M. and Walbot, V. (1993) *The Maize Handbook*. Springer-Verlag, New York; Gottschalk, W. and Wolff, G. (1983) *Induced Mutations in Plant Breeding*. Springer-Verlag, Berlin Heidelberg.

The Id gene maps near the kernel pigmentation gene, Bz2, on chromosome 1. A mutable allele of the Bz2 gene, bz2-m, is the result of an insertion of a Ds2 transposon at this locus. Dooner, et al. (1985) *Mol. Gen. Genetics* 200:240–246. (Ds2 is a defective derivative of the Ac/Ds family of transposable elements and is able to transpose only in the presence of an Ac element which provides transposase.) Taking advantage of the proximity of Id to bz2-m, and the fact that Ac/Ds elements transpose preferentially to linked sites, Applicants selected for id mutants from germinal revertants in the bz2-m population; i.e., by selecting for completely purple kernels that resulted from germinal excision of the Ds2 element (i.e., bz2-m to Bz2), an F1 population with the Ds2 element inserted elsewhere was generated. From an F2 population of these revertants one id mutant was isolated from 600 families examined and designated id*. Crosses of id* to known alleles of id (id-R, for example) confirmed that it is allelic to the id mutation on chromosome 1.

EXAMPLE 2

DNA ANALYSIS:

All molecular biological procedures were performed essentially as described in Sambrook, J., et al. (1989) *Molecular Cloning—A Laboratory Manual*, Cold Spring Harbor Laboratory Press, Cold Spring Harbor, N.Y. Methods for the analysis of maize DNA and RNA were done according to Freeling, M. and Walbot, V. (1993) supra.

For Southern blot analysis, 2–4 mg of maize DNA extracted from leaves was restricted with SacI and electrophoresed on a 1% agarose gel prior to transfer onto Nitrocellulose membranes. For Ds2 probing, an internal 108 bp fragment of the Ds2 transposon was isolated from a plasmid carrying this portion of Ds2 and cut with restriction enzymes BamHI and EcoRI. This fragment was purified from a low melting point agarose gel and radioisotope-containing nucleotides (32P-dATP and 32P-dGTP) were incorporated into the fragment by random primed labeling using a kit from Boehringer-Mannheim. The labeled fragment was used to probe Southern blots using standard formamide hybridization solutions containing 10% dextran sulfate.

To isolate the Ds2-hybridizing 4.2 kb SacI fragment, 100 μg of DNA from a single plant was digested with SacI and electrophoresed on a 1% low-melting agarose gel. A region of the gel between 4 and 5 kb, marked by side markers, was excised from the gel and the DNA contained within the fragment was purified. The DNA was ligated (T4 DNA Ligase, New England Biolabs) into the plasmid vector pLITMUS29 (New England Biolabs) that had been cut with SacI and phosphatase treated (Shrimp Alkaline Phosphatase, U.S. Biochemical) to remove 5' phosphate groups to prevent self ligation. Recombinant plasmids were transformed into the *E. coli* DH10B cells by electroporation and plated on L-agar plates containing 100 μg/ml ampicillin. Approximately 60,000 ampicillin-resistant colonies were grown up on plates and then replica transferred to nitrocellulose membranes. Colonies on filters were lysed and their DNA fixed to the membrane. To determine which colonies carried a recombinant plasmid that hybridized to the Ds2 element, the filters were probed with a labeled Ds2 fragment probe. Hake, et al. (1989) *EMBO J.*, 8:15–22. One colony from 60,000 screened was found to have a plasmid that had a Ds2 element. Restriction analysis of this recombinant plasmid revealed approximately 2.9 kb of genomic DNA to one side of the 1.3 kb Ds2 element and 165 bp on the other side. Sequence analysis of a portion of the flanking DNA was performed by using primers that hybridized to sequence within the plasmid vector and within the Ds2 element itself. The dideoxy chain termination sequencing method was used to sequence double-stranded plasmid DNA.

EXAMPLE 3
RNA ANALYSIS:

Northern blot analysis of polyA RNA from various maize tissues was performed using the 165 bp genomic DNA region to the right flank of the Ds2 element as a probe. RNA was extracted from apical meristem tissue, young and old leaf tissue and from root tips, and 1 µg of each poly A+ mRNA from each sample electrophoresed on a 1.1% agarose gel containing formaldehyde and then transferred to Gene-screen nylon membranes. The 165 bp fragment was labeled as described above, and used to probe the blots.

EXAMPLE 4
DETERMINATION OF THE Id GENE SEQUENCE FROM THE ISOLATED GENOMIC CLONE:

The genomic clone was sequenced by the dideoxy method as described in Sambrook, et al., supra. The strategy used was called "primer walking". Oligonucleotide primers which hybridize to the plasmid vector were used to obtain initial sequence data for the ends of the fragment. This sequence data was then used to synthesize new primers within the sequenced region, which enabled further sequencing into the genomic clone in a reiterative process until the entire fragment was sequenced. Approximately 200 to 350 bp of sequence was read from each primer.

To obtain more of the id gene (specifically the portion from base pairs 1 to 746), a lambda genomic library containing a partial digest of Sau3A-digested B73 DNA was screened with a probe derived from a portion of the 2.9 kb genomic clone. Approximately one million phage from the library were plated, transferred to nitrocellulose filters and probed with a fragment of DNA derived from the right end of the 2.9 kb SacI genomic clone that was labelled as described previously. One phage clone that hybridized to the probe was digested and sub-cloned into the pLITMUS29 plasmid vector. A 3.7 kb BamHI fragment, which included the 2.9 kb genomic region already isolated, was further analyzed by sequencing. An additional 746 bp region containing the 5' end of the id gene was isolated.

EXAMPLE 5
IDENTIFICATION AND ISOLATION OF REGULATORY GENES FROM OTHER PLANT SPECIES:

To identify and isolate regulatory genes in other species of plants which are homologous to the Id gene, the DNA sequence encoding the Id ORF or another fragment of the Id gene, such as one of the zinc-finger regions is used as a probe to screen plant cDNA libraries made of mRNA derived from tissues which express regulatory genes (Sambrook, et al. (1989) supra; Freeling and Walbot (1993) supra) . cDNA libraries constructed from mRNA derived from seedlings and from immature inflorescence tissue are especially likely to contain these genes. Similar libraries from maize have been used successfully by Applicants to obtain cDNA clones of maize cell division cycles genes, such as cdc2 (Colasanti, et al. (1991) *PNAS*, 88:3377–3381) and the cyclins (Renaudin, et al. (1994) *PNAS*, 91:7375–7379) by using short DNA probes for these genes. Clones which hybridize with the radioactive probes are identified and isolated, and a sequence analysis performed by standard methods as described in Sambrook, et al., supra.

EQUIVALENTS

Those skilled in the art will recognize, or be able to ascertain using no more than routine experimentation, many equivalents to the specific embodiments of the invention described specifically herein. Such equivalents are intended to be encompassed in the scope of the following claims.

We claim:

1. Isolated DNA comprising SEQ ID NO:1 or its complement.

2. Isolated DNA which:
 a) hybridizes under conditions of high stringency to the DNA of claim 1;
 b) encodes a polypeptide comprising SEQ ID NO:2; or
 c) has more than one of these characteristics.

3. Isolated DNA consisting of a nucleic acid sequence selected from the group consisting of:
 a) nucleotides 392 to 454 of SEQ ID NO:1;
 b) the complement of nucleotides 392 to 454 of SEQ ID NO:1;
 c) nucleotides 814 to 876 of SEQ ID NO:1; and
 d) the complement of nucleotides 814 to 876 of SEQ ID NO:1.

4. Isolated RNA encoded by the isolated DNA of claim 1.

5. Isolated DNA complementary to an isolated DNA encoding an Id polypeptide the isolated DNA comprising 100 or more consecutive nucleotides of SEQ ID NO:1.

6. Isolated DNA of a plant which
 hybridizes under high stringency conditions To nucleotides 392 to 454 of SEQ ID NO:1 or nucleotides 814 to 876 of SEQ ID NO:1.

7. An isolated Id gene encoding a polypeptide comprising SEQ ID NO:2.

8. A transgenic plant, plant part, plant cell or tissue culture, each of which is transformed with an isolated nucleic acid selected from the group consisting of:
 a) SEQ ID NO:1 or its complement;
 b) nucleotides 392 to 454 of SEQ ID NO:1 or the complement of nucleotides 392 to 454 of SEQ ID NO:1 or nucleotides 814 to 876 of SEQ ID NO:1 or the complement of nucleotides 814 to 876 of SEQ ID NO:1;
 c) a nucleic acid that hybridizes under conditions of high stringency to the DNA of claim 7;
 d) an isolated nucleic acid encoding a polypeptide comprising SEQ ID NO:2;
 e) DNA comprising a maize Id antisense construct;
 f) DNA encoding a dominant-negative mutant maize Id protein; and
 g) DNA which has more than one of the above characteristics.

9. A transgenic seed of a plant of claim 8.

10. A transgenic tissue culture of the plant, plant part, plant cell or tissue culture of claim 8.

11. A transgenic plant, plant part, plant cell or tissue culture according to claim 8 wherein the plant is maize or sorghum or the plant part, plant cell or tissue culture is derived from maize or sorghum.

12. The seed according to claim 9 wherein the seed is a maize or sorghum seed.

13. A tissue culture according to claim 10 wherein the tissue is maize or sorghum tissue.

14. A transgenic plant, plant part, plant cell, or tissue culture of claim 8, wherein the transgenic plant or plant part of claim 8, or the transgenic plant to plant part regenerated from the plant cell or tissue culture of claim 8, exhibits delayed or inhibited time of flower induction compared to an untransformed plant or plant part of the same variety, and where said isolated nucleic acid does not adversely affect the overall health and vigor of the transgenic plant, plant part, plant cell or tissue culture.

15. The transgenic plant, plant part, plant cell or tissue culture according to claim 14 wherein the plant is maize or sorghum or the plant part, plant cell or tissue culture is derived from maize or sorghum.

16. A method of producing a transgenic plant having a delayed or inhibited time of flower induction, comprising introducing into one or more plant cells an isolated nucleic acid selected from the group consisting of:
 a) SEQ ID NO:1 or its complement;
 b) a nucleic acid that hybridizes under conditions of high stringency to the DNA of claim 1; and
 c) a nucleic acid that encodes a polypeptide comprising SEQ ID NO:2; and maintaining the one or more plant cells containing the nucleic acid under conditions appropriate for growth and differentiation of the one or more plant cells, whereby a plant having a delayed or inhibited time of floral induction is produced and wherein the isolated nucleic acid does not otherwise adversely affect the overall health and vigor of said transgenic plant.

17. The method of claim 16 wherein the transgenic plant is selected from the group consisting of: angiosperms, gymnosperms, monocots and dicots.

18. A method of producing a transgenic plant exhibiting a delayed or inhibited time of flower induction, the method comprising introducing into one or more plant cells an isolated nucleic acid selected from the group consisting of
   a) SEQ ID NO:1 or its complement;
   b) a nucleic acid that hybridizes under conditions of high stringency to the DNA of claim 1; and
   c) a nucleic acid that encodes a polypeptide comprising SEQ ID NO:2.

19. A transgenic plant, transgenic plant part, transgenic plant cell, or transgenic tissue culture, each containing 100 or more consecutive nucleotides of SEQ ID NO:1, wherein the 100 or more consecutive nucleotides of SEQ ID NO:1 delays or inhibits the time of flower induction.

20. The plant, plant part, plant cell or tissue culture according to claim 19 wherein the plant is maize or sorghum; or the plant part, plant cell or tissue culture is derived from maize or sorghum.

* * * * *

SEQUENCE LISTING

```
<160> NUMBER OF SEQ ID NOS: 20

<210> SEQ ID NO 1
<211> LENGTH: 3693
<212> TYPE: DNA
<213> ORGANISM: Zea mays
<220> FEATURE:
<221> NAME/KEY: misc_feature
<222> LOCATION: (241)...(329)
<223> OTHER INFORMATION: intron
<220> FEATURE:
<221> NAME/KEY: misc_feature
<222> LOCATION: (628)...(746)
<223> OTHER INFORMATION: intron
<220> FEATURE:
<221> NAME/KEY: misc_feature
<222> LOCATION: (921)...(2347)
<223> OTHER INFORMATION: intron
<220> FEATURE:
<221> NAME/KEY: misc_feature
<222> LOCATION: (1)...(3693)
<223> OTHER INFORMATION: n = A, T, C or G
<220> FEATURE:
<221> NAME/KEY: misc_feature
<222> LOCATION: (1)...(3693)
<223> OTHER INFORMATION: n = A,T,C or G

<400> SEQUENCE: 1
gacgacagac g atg cag atg atg atg ctc tct gat ctc tcg tct gac gac      50
```

-continued

```
cac gag gcc act gga tcc agc tcc tat ggc ggg gac atg gcc agc tac        98
gcc ctc agc cct ctc ttc ctc gca ccg gcg gcc tcg gcc acc gcg ccg       146
ctg ccg cca cct ccg cag ccg ccg gcc gag gag ctc acc aac aag cag       194
gcc gcg ggc ggc ggc aag agg aag aga agc cag ccg ggg aac cca ggt       242
acg tag tag tta att ggc tga cca atc acg ccg acc gat gca cct aat       290
taa tga atc aat gtg cta caa ata aat taa aac caa aag acc ccg gcg       338
cgg agg tga tcg cgc tgt cgc cgc gca cgc tgg tgg cga cga acc ggt       386
tcg tgt gcg aga tct gca aca agg ggt tcc agc ggg acc aga acc tgc       434
agc tgc acc gcc ggg gcc aca acc tcc cct gga agc tcc gcc agc gca       482
gca gcc tcg tcg tcc cgt cgt cgt cgg cgg cgg cag gct ccg gcg gca       530
ggc agc agc agc agc agg gcg agg ccg cgc cga cgc cgc cgc gta agc       578
gcg tct acg tct gcc ccg agc cca cgt gcg tgc acc acg acc cgg cga       626
ggt acg tat gca cgg tcc tgc tcc tgc ata tat gcg agg gaa tgc tag       674
cga cat agc ata aca tct cat cga tcc atc cat cca tcc atc cat cca       722
tcc atc cat cca tcc atc cat cag agc tct ggg gga ctt gac tgg gat       770
caa gaa gca ctt ctc gcg gaa gca cgg gga gaa gcg gtg gtg ctg cga       818
gcg ctg cgg gaa gcg cta cgc cgt gca gtc gga ctg gaa ggc gca cgt       866
caa ggg gtg tgg cac gcg cga gta ccg ctg cga ctg cgg cat cct ctt       914
ctc cag gta cat ctc atc tca tga tca ccg tgc aca tat gca tgg acg       962
acg tgt gct ttg ctg taa ttg taa acg ctg atc att ttt act aac aac      1010
cat gct gga tat aat agc cta atc tct cac cgg acg gat cga gag aaa      1058
acc tag cta gac ggg atc gat cgg tcc agc agg ttg ccg ccg acg act      1106
gtt cca tcg atc gag cct gtt aat tta gtc ata aaa agg atc gag cat      1154
atg cat gta tat gaa cta tct tcc ttc act gac caa cat cat atc atg      1202
cat gga gct agc tag tta atc agt aca tat act cct ata tat aca tag      1250
gtt ttc aag aac agt ggg tga ttc tga agc aac cta aat ata tat aga      1298
tac caa aaa ana tat gaa gtc atc agc acg atc tgc gag cgg gta cgg      1346
ttc ttg aac tct tct gat ggt tgc agt aat acc ggc caa caa aaa tat      1394
att ata tat tta tcg tcc gct agt tga ttt tta aac taa atg cgc act      1442
gat aaa aaa aga agg gtt gga gta cta tat ata caa gag cat gtg gcc      1490
ttc agt tac aat ttt agg gtt tcc atg cat cct gtc ata aaa cta ttt      1538
gca tga tca cat ccc tat ata tcg gga tac tac tgt tgt gaa aaa acc      1586
atg agt ccc tgg tca aac cag tat atg tac atg caa tat gtt tat tgc      1634
atg cat att tgg gaa tga aca tcc tct gcc tgc acc aac ttt atg gca      1682
gta cgt cca tgt ggc cat cat gac aca ttc cct tca aaa atg gaa cat      1730
ata tag cta cag cat atg aag caa ttg aag agt act tta att gtg aaa      1778
tag tac tac tgc aag tat ata tat atg tag tag cac aac agt cga ata      1826
atg cag tgc att aga tat agt agt gaa gtt aag agt tag ttt cca aat      1874
ctt tta cta gag aga gca taa aaa atc tat aaa aaa ttc taa ttc aac      1922
```

-continued

```
ttc taa tgt atc tta tgt taa gaa agg ggt ata tat aaa aag agt aaa      1970
ttc tgt cat tag ata cat cgt tag cag tag tac cac tga att taa tta      2018
cgt cct ata cac acg cgc aca cac atg cat gca tgc atc tgc atg ctt      2066
ctt ttc agt agt gat cac aaa gga aac tga caa aag aac cta gct aat      2114
cat agg acg cag ctt ttc gtc agc aaa gtt aaa cga aac ttt aca tgc      2162
atg gat tgc att gag tac tca cgc atg tgc acg tca aca cgc gca cac      2210
ata tag tat att aac ata gta ctt tat ata cca act aat taa taa agt      2258
cat tga ctc ctc tgt cct ctg gtc att tgt tta gct aat taa ccc gtt      2306
tcg ttt gat gca tgc atg gtc tct ctg gcg tgg tcg tgc agg aag gac      2354
agc ctg ctc acg cac agg gcc ttc tgc gat gcc cta gca gag gag agc      2402
gcg agg ctt ctt gca gca gca aac aac ggc agc act atc acc acg           2450
acc agc agc agc aac aac aat gat ctt ctc aac gcc agc aat aat atc      2498
acg cca tta ttc ctc ccg ttc gcc agc tct cct cct cct gtc gtc gta      2546
gcg gcg gca caa aac cct aat aac acc ctc ttc ttc ctg cac caa gag      2594
ctg tcc ccc ttc ctg caa ccg agg gtg acg atg caa caa caa ccc tcg      2642
ccc tat ctt gac ctc cat atg cac gtc gac gcc agc atc gtc acc acc      2690
acc ggt ggt ctc gcg gac ggc acg ccg gtc agc ttt ggc ctc gct ctg      2738
gac ggc tcg gtg gcc acc gtc ggc cac cgg cgc ctc act agg gac ttc      2786
ctc ggt gtc gat ggt ggc ggt cgt cag gtc gag gag ctg cag ctt cca      2834
ctg tgc gcc aca gca gcc gca gca ggt gcc agc cgc acc gcc agc tgc      2882
gcc acc gac ctg aca agg cag tgc ctc ggc ggc cgg ctg ccg ccg gtc      2930
aac gag acc tgg agc cac aac ttc tag gcccgctata tacttcaagc            2977
tgcattgaga ctttgagaga cgaatgaacg gaacacccaa actgcatgca ctctagcttg    3037
aagagcaaac caaaactgga gtagcaagta tggtgcacta ctgttgttaa tttaccttaa    3097
tttattgatc tctggttagt tctgttttca tttagggcaa tgcgggctag ctaattaatt    3157
cgatgtgcac aacttttgat gaatggacca taaagtttat cttgttgctt ttttttttgtt   3217
tgattatgtt tcgctgcaca cccatgtgtt ctcataatgg tatgtcgaaa gaaatagatg    3277
atatactaat ataccatat cagtctaaac aacatgaata aagattcaat caagaggagt     3337
ggcacatgca tggttactga tggtggtacg gagtcatcga taagtggtag tggaggaaaa    3397
gcttggtgca aacggcgatg aatacaacga cacgtatagc accgtttaac ttggatgaaa    3457
gacgactcgt cgtggaagtt gagagcagtc atgcaaagaa cactttccaa aaaccttatt   3517
aaatatgtcc tctatctgtg caaggttaga aagatgagaa ttatggagat ctactctcct   3577
gaatcctgat tggtgatgca cgtaaatgct caggatgaag aggctatgac gtcagtgcaa    3637
cattgagaag tgaaaaatac taatttatat cttaagattt ttcaaagtag gagctc        3693
```

<210> SEQ ID NO 2
<211> LENGTH: 436
<212> TYPE: PRT
<213> ORGANISM: Zea mays

<400> SEQUENCE: 2

Met Gln Met Met Met Leu Ser Asp Leu Ser Ser Asp Asp His Glu Ala
 1               5                  10                  15

-continued

```
Thr Gly Ser Ser Ser Tyr Gly Gly Asp Met Ala Ser Tyr Ala Leu Ser
             20                  25                  30

Pro Leu Phe Leu Ala Pro Ala Ala Ser Ala Thr Ala Pro Leu Pro Pro
             35                  40                  45

Pro Pro Gln Pro Pro Ala Glu Glu Leu Thr Asn Lys Gln Ala Ala Gly
 50                  55                  60

Gly Gly Lys Arg Lys Arg Ser Gln Pro Gly Asn Pro Asp Pro Gly Ala
 65                  70                  75                  80

Glu Val Ile Ala Leu Ser Pro Arg Thr Leu Val Ala Thr Asn Arg Phe
                 85                  90                  95

Val Cys Glu Ile Cys Asn Lys Gly Phe Gln Arg Asp Gln Asn Leu Gln
                100                 105                 110

Leu His Arg Arg Gly His Asn Leu Pro Trp Lys Leu Arg Gln Arg Ser
             115                 120                 125

Ser Leu Val Val Pro Ser Ser Ala Ala Gly Ser Gly Gly Arg
             130                 135                 140

Gln Gln Gln Gln Gly Glu Ala Ala Pro Thr Pro Pro Arg Lys Arg
145                 150                 155                 160

Val Tyr Val Cys Pro Glu Pro Thr Cys Val His His Asp Pro Ala Arg
                165                 170                 175

Ala Leu Gly Asp Leu Thr Gly Ile Lys Lys His Phe Ser Arg Lys His
             180                 185                 190

Gly Glu Lys Arg Trp Cys Cys Glu Arg Cys Gly Lys Arg Tyr Ala Val
             195                 200                 205

Gln Ser Asp Trp Lys Ala His Val Lys Gly Cys Gly Thr Arg Glu Tyr
             210                 215                 220

Arg Cys Asp Cys Gly Ile Leu Phe Ser Arg Lys Asp Ser Leu Leu Thr
225                 230                 235                 240

His Arg Ala Phe Cys Asp Ala Leu Ala Glu Glu Ser Ala Arg Leu Leu
             245                 250                 255

Ala Ala Ala Ala Asn Asn Gly Ser Thr Ile Thr Thr Thr Ser Ser Ser
             260                 265                 270

Asn Asn Asn Asp Leu Leu Asn Ala Ser Asn Asn Ile Thr Pro Leu Phe
             275                 280                 285

Leu Pro Phe Ala Ser Ser Pro Pro Val Val Ala Ala Ala Gln
 290                 295                 300

Asn Pro Asn Asn Thr Leu Phe Phe Leu His Gln Glu Leu Ser Pro Phe
305                 310                 315                 320

Leu Gln Pro Arg Val Thr Met Gln Gln Gln Pro Ser Pro Tyr Leu Asp
             325                 330                 335

Leu His Met His Val Asp Ala Ser Ile Val Thr Thr Gly Gly Leu
             340                 345                 350

Ala Asp Gly Thr Pro Val Ser Phe Gly Leu Ala Leu Asp Gly Ser Val
             355                 360                 365

Ala Thr Val Gly His Arg Arg Leu Thr Arg Asp Phe Leu Gly Val Asp
             370                 375                 380

Gly Gly Gly Arg Gln Val Glu Glu Leu Gln Leu Pro Leu Cys Ala Thr
385                 390                 395                 400

Ala Ala Ala Ala Gly Ala Ser Arg Thr Ala Ser Cys Ala Thr Asp Leu
                405                 410                 415

Thr Arg Gln Cys Leu Gly Gly Arg Leu Pro Pro Val Asn Glu Thr Trp
             420                 425                 430

Ser His Asn Phe
```

<210> SEQ ID NO 3
<211> LENGTH: 415
<212> TYPE: DNA
<213> ORGANISM: Zea mays

<400> SEQUENCE: 3

```
gagctctggg ggacttgact gggatcaaga agcacttctc gcggaagcac ggggagaagc      60
ggtggtgctg cgagcgctgc gggaagcgct acgccgtgca gtcggactgg aaggcgcacg     120
tcaagggtg tggcacgcgc gagtaccgct gcgactgcgg catcctcttc tccaggtaca      180
tctcatctca tgatcaccgt gcacatatgc atggacgacg tgtgctttgc tgtaattgta     240
aacgctgatc atttttacta caaccatgc tggatataat agcctaatct ctcaccggac      300
ggatcgagag aaaacctagc tagacgggat cgatcggtcc agcaggttgc cgccgacgac     360
tgttccatcg atcgagcctg ttaatttagt cataaaaagg atcgagcata tgcat          415
```

<210> SEQ ID NO 4
<211> LENGTH: 58
<212> TYPE: PRT
<213> ORGANISM: Zea mays

<400> SEQUENCE: 4

```
Ala Leu Gly Asp Leu Thr Gly Ile Lys Lys His Phe Ser Arg Lys His
 1               5                  10                  15

Gly Glu Lys Arg Trp Cys Cys Glu Arg Cys Gly Lys Arg Tyr Ala Val
            20                  25                  30

Gln Ser Asp Trp Lys Ala His Val Lys Gly Cys Gly Thr Arg Glu Tyr
        35                  40                  45

Arg Cys Asp Cys Gly Ile Leu Phe Ser Arg
    50                  55
```

<210> SEQ ID NO 5
<211> LENGTH: 17
<212> TYPE: PRT
<213> ORGANISM: Drosophila

<400> SEQUENCE: 5

```
His Phe Ser Asn Pro Ala Leu Asn Arg Arg Trp Val Cys His Ala Cys
 1               5                  10                  15

Gly
```

<210> SEQ ID NO 6
<211> LENGTH: 28
<212> TYPE: PRT
<213> ORGANISM: Maize ORF

<400> SEQUENCE: 6

```
Ala Leu Gly Asp Leu Thr Gly Ile Lys Lys His Phe Ser Arg Lys His
 1               5                  10                  15

Gly Glu Lys Arg Trp Cys Cys Glu Arg Cys Gly Lys
            20                  25
```

<210> SEQ ID NO 7
<211> LENGTH: 18
<212> TYPE: PRT
<213> ORGANISM: Xenopus laevis

<400> SEQUENCE: 7

His Leu Lys Leu His Lys Gly Glu Lys Pro Phe Pro Cys Ser Gln Cys
1               5                  10                  15

Gly Lys

<210> SEQ ID NO 8
<211> LENGTH: 27
<212> TYPE: PRT
<213> ORGANISM: Homo sapiens

<400> SEQUENCE: 8

Ala Tyr Ser Arg Leu Glu Asn Leu Lys Thr His Leu Arg Ser His Thr
1               5                  10                  15

Gly Glu Lys Pro Tyr Val Cys Glu His Glu Gly
            20                  25

<210> SEQ ID NO 9
<211> LENGTH: 19
<212> TYPE: PRT
<213> ORGANISM: Mus musculus

<400> SEQUENCE: 9

Lys His Lys Lys Ile His Lys Gly Gln Gln Tyr Tyr Thr Cys Arg Asp
1               5                  10                  15

Cys Glu Lys

<210> SEQ ID NO 10
<211> LENGTH: 27
<212> TYPE: DNA
<213> ORGANISM: Zea mays
<220> FEATURE:
<221> NAME/KEY: misc_feature
<222> LOCATION: (19)...(19)
<223> OTHER INFORMATION: 'N' at position 19 represents the insertion
      site of the DS2 transposon.
<220> FEATURE:
<221> NAME/KEY: misc_feature
<222> LOCATION: (1)...(27)
<223> OTHER INFORMATION: n = A,T,C or G

<400> SEQUENCE: 10
ggcatcctct tctccaggnt ctccagg                                          27

<210> SEQ ID NO 11
<211> LENGTH: 26
<212> TYPE: DNA
<213> ORGANISM: Zea mays
<220> FEATURE:
<221> NAME/KEY: misc_feature
<222> LOCATION: (18)...(18)
<223> OTHER INFORMATION: 'N' at position 18 represents an insertion of 7
      nucleotides, producing a mutation.
<220> FEATURE:
<221> NAME/KEY: misc_feature
<222> LOCATION: (1)...(26)
<223> OTHER INFORMATION: n = A,T,C or G

<400> SEQUENCE: 11
ggcatcctct tctccagnac tccagg                                           26

<210> SEQ ID NO 12
<211> LENGTH: 8
<212> TYPE: PRT
<213> ORGANISM: Zea mays

<400> SEQUENCE: 12

Gly Ile Leu Phe Ser Arg Leu Gln

```
<210> SEQ ID NO 13
<211> LENGTH: 24
<212> TYPE: DNA
<213> ORGANISM: Zea mays
<220> FEATURE:
<221> NAME/KEY: misc_feature
<222> LOCATION: (16)...(16)
<223> OTHER INFORMATION: 'N' at position 16 represents an insertion of 5
      nucleotides, producing a mutation.
<220> FEATURE:
<221> NAME/KEY: misc_feature
<222> LOCATION: (1)...(24)
<223> OTHER INFORMATION: n = A,T,C or G

<400> SEQUENCE: 13
ggcatcctct tctccnactc cagg                                            24

<210> SEQ ID NO 14
<211> LENGTH: 7
<212> TYPE: PRT
<213> ORGANISM: Zea mays

<400> SEQUENCE: 14

Gly Ile Leu Phe Ser Thr Pro
 1               5

<210> SEQ ID NO 15
<211> LENGTH: 14
<212> TYPE: DNA
<213> ORGANISM: Zea mays

<400> SEQUENCE: 15
ggcatcctct tctc                                                       14

<210> SEQ ID NO 16
<211> LENGTH: 4
<212> TYPE: PRT
<213> ORGANISM: Zea mays

<400> SEQUENCE: 16

Gly Ile Leu Phe
 1

<210> SEQ ID NO 17
<211> LENGTH: 22
<212> TYPE: DNA
<213> ORGANISM: Zea mays
<220> FEATURE:
<221> NAME/KEY: misc_feature
<222> LOCATION: (16)...(16)
<223> OTHER INFORMATION: 'N' at position 16 represents an insertion of 3
      nucleotides, producing a mutation.
<220> FEATURE:
<221> NAME/KEY: misc_feature
<222> LOCATION: (1)...(22)
<223> OTHER INFORMATION: n = A,T,C or G

<400> SEQUENCE: 17
ggcatcctct tctccntcca gg                                              22

<210> SEQ ID NO 18
<211> LENGTH: 7
<212> TYPE: PRT
<213> ORGANISM: Zea mays

<400> SEQUENCE: 18
```

```
-continued

Gly Ile Leu Phe Ser Ser Arg
 1               5

<210> SEQ ID NO 19
<211> LENGTH: 24
<212> TYPE: DNA
<213> ORGANISM: Zea mays

<400> SEQUENCE: 19
ggcatcctct tctccaggaa ggac                                           24

<210> SEQ ID NO 20
<211> LENGTH: 8
<212> TYPE: PRT
<213> ORGANISM: Zea mays

<400> SEQUENCE: 20

Gly Ile Leu Phe Ser Arg Lys Asp
 1               5
```